United States Patent
Crozet

(10) Patent No.: US 8,840,666 B2
(45) Date of Patent: *Sep. 23, 2014

(54) TWO PART INTERSOMATIC IMPLANT

(75) Inventor: Yves Crozet, Bellach (CH)

(73) Assignee: Stryker France (FR)

( * ) Notice: Subject to any disclaimer, the term of this patent is extended or adjusted under 35 U.S.C. 154(b) by 1567 days.
This patent is subject to a terminal disclaimer.

(21) Appl. No.: 11/192,578

(22) Filed: Jul. 29, 2005

(65) Prior Publication Data

US 2005/0273168 A1  Dec. 8, 2005

Related U.S. Application Data

(63) Continuation of application No. 10/192,457, filed on Jul. 10, 2002, now Pat. No. 7,056,341, which is a continuation of application No. 10/131,741, filed on Apr. 23, 2002, now Pat. No. 6,855,168, which is a continuation of application No. 09/403,396, filed as application No. PCT/FR98/00825 on Apr. 24, 1998, now abandoned.

(30) Foreign Application Priority Data

Apr. 25, 1997 (FR) ...................................... 97 05137
Nov. 12, 1997 (FR) ...................................... 97 14150

(51) Int. Cl.
| | | |
|---|---|---|
| *A61F 2/44* | (2006.01) | |
| *A61B 17/86* | (2006.01) | |
| *A61F 2/30* | (2006.01) | |
| *A61F 2/46* | (2006.01) | |
| *A61F 2/28* | (2006.01) | |
| *A61B 17/88* | (2006.01) | |

(52) U.S. Cl.
CPC ....... *A61F 2/4455* (2013.01); *A61F 2220/0025* (2013.01); *A61F 2230/0006* (2013.01); *A61F 2230/0034* (2013.01); *A61F 2310/00023* (2013.01); *A61F 2/30767* (2013.01); *A61F 2/4611* (2013.01); *A61F 2002/30354* (2013.01); *A61F 2002/30217* (2013.01); *A61F 2002/448* (2013.01); *A61F 2310/00796* (2013.01); *A61F 2002/30879* (2013.01); *A61F 2002/30774* (2013.01); *A61F 2230/0082* (2013.01); *A61F 2/30744* (2013.01); *A61F 2/446* (2013.01);

(Continued)

(58) Field of Classification Search
CPC ....... A61F 2/4455; A61F 2/446; A61F 2/447; A61F 2/4465; A61F 2/44; A61F 2002/30131; A61F 2002/30169; A61F 2002/30772; A61F 2002/30777
USPC ............ 623/17.11–17.16; 411/103, 104, 437, 411/383, 385
See application file for complete search history.

(56) References Cited

U.S. PATENT DOCUMENTS

| | | |
|---|---|---|
| 1,282,538 A | 10/1918 | Cadwallader |
| 2,677,369 A | 5/1954 | Knowles |

(Continued)

FOREIGN PATENT DOCUMENTS

| | | |
|---|---|---|
| DE | 40 12 622 C1 | 7/1991 |
| DE | 44 16 605 C1 | 6/1995 |

(Continued)

OTHER PUBLICATIONS

European Search Report, EP 10184617 dated Jan. 12, 2011.

*Primary Examiner* — Brian Pellegrino

(74) *Attorney, Agent, or Firm* — Lerner, David, Littenberg, Krumholz & Mentlik, LLP

(57) ABSTRACT

A spinal implant includes a hollow body having a pair of lateral braches extending from a leading end to a trailing end of the hollow body. The branches have opposing concave, non-threaded inner surfaces defining an internal space of the hollow body and outer surfaces defining an outer dimension of the hollow body. The hollow body has upper and lower faces extending between leading and trailing ends thereof. At least one of the lateral branches has a first opening extending between the outer and inner surfaces thereof, and a second opening located outside the internal space of the hollow body and extending between the upper and lower faces, the first and second openings being in communication with one another. The implant also includes an anchoring member insertible between the lateral branches and into the internal space of the hollow body, whereby the concave inner surfaces of the lateral branches substantially conform to the outer diameter of the anchoring member.

23 Claims, 29 Drawing Sheets

(52) U.S. Cl.
CPC .............. *A61F 2002/30143* (2013.01); *A61F 2002/30373* (2013.01); *A61F 2230/0067* (2013.01); *A61F 2002/30364* (2013.01); *A61F 2002/30772* (2013.01); *A61F 2002/30271* (2013.01); *A61F 2002/30131* (2013.01); *A61F 2002/30797* (2013.01); *A61F 2002/30233* (2013.01); *A61F 2230/0013* (2013.01); *A61F 2002/2835* (2013.01); *A61F 2230/0047* (2013.01); *A61F 2230/0017* (2013.01); *A61B 17/861* (2013.01); *A61F 2002/305* (2013.01); *A61B 17/8625* (2013.01); *A61F 2002/30777* (2013.01); *A61F 2002/30224* (2013.01); *A61F 2002/30405* (2013.01); *A61F 2002/30616* (2013.01); *A61F 2002/30904* (2013.01); *A61F 2230/0069* (2013.01); *A61F 2002/3085* (2013.01); *A61F 2/442* (2013.01); *A61F 2002/30367* (2013.01); *A61F 2002/30235* (2013.01); *A61F 2002/30187* (2013.01); *A61F 2002/30169* (2013.01); *A61F 2/447* (2013.01); *A61B 17/8875* (2013.01); *A61F 2310/00017* (2013.01); *A61B 17/8645* (2013.01); *A61F 2002/4475* (2013.01); *A61B 17/86* (2013.01); *A61F 2220/0033* (2013.01); *A61B 17/864* (2013.01); *A61F 2002/30118* (2013.01); *A61F 2002/30848* (2013.01)
USPC ...................................... 623/17.11

(56) References Cited

U.S. PATENT DOCUMENTS

| | | | |
|---|---|---|---|
| 4,834,757 A | 5/1989 | Brantigan | |
| 4,863,476 A | 9/1989 | Shepperd | |
| 4,936,851 A | 6/1990 | Fox et al. | |
| 5,192,327 A | 3/1993 | Brantigan | |
| 5,217,497 A | 6/1993 | Mehdian | |
| 5,306,307 A | 4/1994 | Senter et al. | |
| 5,458,638 A | 10/1995 | Kuslich et al. | |
| 5,487,742 A | 1/1996 | Cotrel | |
| 5,609,635 A | 3/1997 | Michelson | |
| 5,609,636 A | 3/1997 | Kohrs et al. | |
| 5,665,122 A | 9/1997 | Kambin | |
| 5,683,394 A | 11/1997 | Rinner | |
| 5,766,251 A | 6/1998 | Koshino | |
| 5,776,198 A | 7/1998 | Rabbe et al. | |
| 5,776,199 A | 7/1998 | Michelson | |
| 5,800,550 A | 9/1998 | Sertich | |
| 5,860,973 A | 1/1999 | Michelson | |
| 5,861,041 A | 1/1999 | Tienboon et al. | |
| 5,865,845 A | 2/1999 | Thalgott | |
| 5,888,223 A | 3/1999 | Bray, Jr. | |
| 5,951,553 A | 9/1999 | Betz et al. | |
| 6,059,829 A | 5/2000 | Schlapfer et al. | |
| 6,129,763 A | 10/2000 | Chauvin et al. | |
| 6,143,031 A * | 11/2000 | Knothe et al. | 623/17.16 |
| 6,224,631 B1 * | 5/2001 | Kohrs | 623/17.11 |
| 6,824,564 B2 | 11/2004 | Crozet et al. | |
| 6,855,168 B2 | 2/2005 | Crozet | |
| 7,056,341 B2 | 6/2006 | Crozet | |

FOREIGN PATENT DOCUMENTS

| | | |
|---|---|---|
| DE | 295 19 418 | 7/1995 |
| DE | 4409392 | 9/1995 |
| DE | 296 12 269 | 7/1996 |
| EP | 0 664 994 | 8/1995 |
| EP | 0 716 840 | 6/1996 |
| EP | 0 732 093 | 9/1996 |
| FR | 2 703 850 | 10/1994 |
| FR | 2 727 003 | 11/1994 |
| FR | 2 710 519 | 4/1995 |
| FR | 2 717 068 | 9/1995 |
| FR | 2718955 A1 | 10/1995 |
| FR | 2 724 312 | 3/1996 |
| FR | 2 727 004 | 5/1996 |
| WO | WO-90/11740 | 10/1990 |
| WO | WO-96/14809 | 5/1996 |
| WO | WO-96 27339 | 9/1996 |
| WO | WO-96/40016 | 12/1996 |
| WO | 9715248 A1 | 5/1997 |
| WO | WO-97 15246 | 5/1997 |
| WO | 98/14142 A1 | 4/1998 |
| WO | WO-98/46173 | 10/1998 |

* cited by examiner

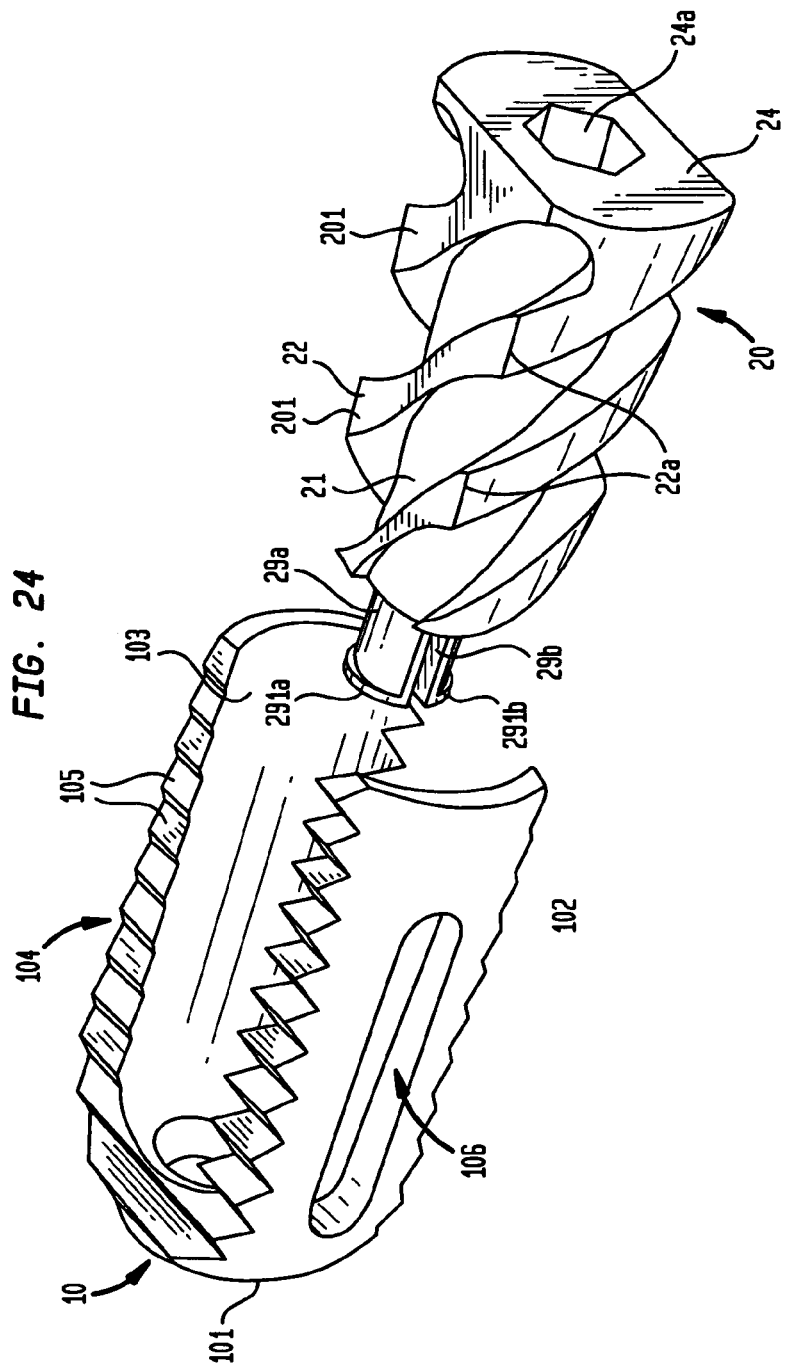

TWO PART INTERSOMATIC IMPLANT

CROSS-REFERENCE TO RELATED APPLICATIONS

The present application is a continuation of U.S. patent application Ser. No. 10/192,457, now U.S. Pat. No. 7,056,341, which is a continuation of U.S. patent application Ser. No. 10/131,741, now U.S. Pat. No. 6,855,168, which is a continuation of U.S. patent application Ser. No. 09/403,396, filed Feb. 15, 2000, now abandoned, which claims priority under 35 U.S.C. 371 of PCT/FR98/00825, filed Apr. 24, 1998, the disclosures of which are hereby incorporated by reference herein.

BACKGROUND OF THE INVENTION

The present invention relates generally to intersomatic implants which can be used in the surgical treatment of the spine.

A great many intersomatic implants are already known. These include, in particular, implants made up of several parts, particularly to give the implants certain deformability characteristics. These known implants have the disadvantage of being more expensive and difficult to manufacture, and more awkward to fit. These implants can also suffer from long-term reliability problems.

In order to overcome some of the above-mentioned disadvantages, certain implants are provided in the form of one-piece hollow bodies, or cages, having roughened areas on their upper and lower faces in order to ensure good initial immobilization relative to the overlying and underlying vertebral plates. The hollow bodies permit bone to grow through the implant for fusing the implant to vertebral bone. One such implant having a hollow body is disclosed in FR-A-2,703,580.

These known one-piece implants, despite the presence of roughened areas which become anchored in the vertebral plates, may suffer from inadequate stability in some cases. This is because the quality of the anchoring, which is effected by a simple translational movement, depends on the hardness of the bones.

Other implants have an outer body and an inner anchorage reinforcement element that is screwed into the outer body. The threads of the anchorage reinforcement element project above and below the upper and lower faces of the outer body.

One object of the present invention is to improve this type of known implant.

SUMMARY OF THE INVENTION

An implant for surgery of the spine includes an essentially hollow body insertable into an intervertebral space defined by opposing vertebrae. The body has a pair of lateral walls enclosing an internal space exposed to the overlying and underlying vertebrae. The implant also includes an anchorage reinforcement member that is screwed into the internal space of the hollow body. The anchorage reinforcement member has external threads or bone anchoring projections having a diameter greater than the overall height of the body. The external threads may be self-tapping screw threads or have a generally square radial cross-section.

To counter the reverse movement of the body out of the intervertebral space, and hence to further improve the securing of the implant in position, the hollow body has upper and lower surfaces provided with sharp-edged teeth which can be anchored in the vertebrae. The teeth preferably have a triangular cross-section.

According to another preferred embodiment of the present invention, in order to improve the compactness of the implant and to make it easier to put into place, the lateral walls of the hollow body are partially cylindrical and coaxial with an axis of the anchorage reinforcement member.

According to yet another preferred embodiment of the invention, the lateral walls have through-openings permitting bone to grow through them. These through-openings preferably include elongate slots extending substantially parallel to the direction of insertion of the anchorage reinforcement member into the hollow body.

In order to give the body a greater width, it is possible to use, for the lateral walls of the body, thick walls in which second through-openings are formed, extending between the upper and lower faces of the body. Bone growth can also be induced between the two vertebral plates via these second through-openings.

The first through-openings preferably bring the internal space into communication with the second through-openings.

It is also possible to provide through-openings which bring the second through-openings into communication with the outer sides of the body.

According to another preferred embodiment of the invention, the hollow body has a distal end wall connecting the lateral walls. The distal end wall is rounded to facilitate insertion of the hollow body into the intervertebral space.

The invention also preferably includes an implant as described above, in which the hollow body has a distal end wall connecting the lateral walls. The distal end wall has a tapped hole for temporarily fixing the hollow body to an instrument for facilitating insertion of the body.

This screw thread of the anchorage reinforcement member preferably has a radial cross-section which changes progressively from an essentially triangular radial cross-section to the generally square radial cross-section starting from the distal end of the thread, whereby the diameter of the screw thread increases progressively, starting from its distal end, up to a part of essentially constant diameter. In other words, the screw thread has a radial cross-section that transforms from a beveled distal end to a substantially square radial cross-section.

According to another preferred embodiment of the invention, an implant is also proposed in which the projections for bone anchorage comprise a screw thread in the form of a helical band encircling an internal space of the anchorage reinforcement member.

The helical band is advantageously connected to a fork extending inside the band in an axial direction of the member, and this fork preferably comprises two branches extending from a proximal end wall of the anchorage reinforcement member.

The fork may also include branches having a frustoconical external surface, the diameter of which decreases from the proximal end towards the distal end of the member. This makes it possible to compress a substance promoting bone growth, placed beforehand in the anchorage reinforcement member, when the latter is being screwed in.

Alternatively, the fork includes at least two branches, each having a cutting edge for cutting or biting into bone, in order thereby to accumulate bone chips inside the member 20 and facilitate bone fusion. It is preferable for the fork and the helical band to be made in one piece.

The invention also proposes an implant in which the projections for bone anchorage include a screw thread, whereby the anchorage reinforcement member has structure for immobilizing the latter against reverse rotation. The immobilizing structure preferably includes a deformed part of the thread in the region of its proximal end, which improves the stability of the implant until fusion has taken place.

According to another preferred embodiment of the present invention, the projections for bone anchorage include a screw thread having an external diameter which decreases from the proximal end toward the distal end in order to make it easier for the screw thread to penetrate the vertebral plates.

In another preferred embodiment, the anchorage reinforcement member has a proximal end wall which is able to essentially close a frontal opening of the hollow body in such a way that a substance for promoting bone growth, placed inside the member, is compressed during the insertion of the member into the hollow body.

In this embodiment, the anchorage reinforcement member has at least one part whose external surface belongs to a truncated cone. Alternatively, the anchorage reinforcement member is substantially shorter than the body and has a generally conical point directed towards the distal end wall of the body.

It is advantageous in this case that the proximal end wall of the member has a tapped opening for temporarily fixing the member to an instrument for inserting the member.

According to yet another preferred embodiment of the present invention, the anchorage reinforcement member has indexing means for fixing the member to an instrument for inserting the member in a given angular relationship.

According to another preferred embodiment, the anchorage reinforcement member has a plug attached at its proximal end. The plug can, for example, be screwed into a tapped frontal opening of the anchorage reinforcement member, or else can be engaged by being clipped elastically into a frontal opening of the anchorage reinforcement member.

The plug preferably has an arrangement which can cooperate with an instrument allowing the member to be driven in rotation, and/or arrangements for angular indexing of the anchorage reinforcement member with an instrument for positioning the member.

It is also proposed according to the invention that the projections for bone anchorage include a screw thread, and that at least one of the lateral branches of the body has a reentrant part forming a threading which is able to cooperate with the thread. This reentrant part can be provided only on one of the branches and can constitute the only part of the body cooperating, by screwing, with the screw thread. In addition, this reentrant part can have an essentially rectilinear free end edge.

According to another preferred embodiment, the invention proposes an implant in which the member is oriented obliquely, for example at about 45°, in relation to a plane of the body corresponding to the sagittal plane.

According to another preferred embodiment, the anchoring member has through-openings provided in the member between the interior and the exterior thereof. The openings are elongate in an essentially circumferential direction of the member.

According to another preferred embodiment of the present invention, the body has a distal end wall, and the anchorage reinforcement member has a distal end part which can be screwed into an opening of the distal end wall.

The body can also have a proximal end wall including an opening which is wider than the external dimension of the anchorage reinforcement member and in which the member can be engaged freely.

The invention furthermore proposes an implant in which the body has a proximal wall, a distal wall and two lateral walls, the walls defining therebetween an internal space which is larger than the anchorage reinforcement member. This assembly increases the space designated for bone growth between the overlying and underlying vertebral plates.

The anchorage reinforcement member may have a threaded part for screwing it into the proximal wall of the body. In other preferred embodiments, the anchorage reinforcement member and the distal wall of the body may have threaded structure cooperating with each other for fixing the member to the body.

In such a configuration, the projections for bone anchorage can comprise a screw thread having the same pitch as the threaded part or the threaded means for fixing to the body.

The shape of the body, in this case, is preferably such that the lateral walls and the proximal wall of the body extend essentially on the same arc of a circle, and that the distal wall is essentially rectilinear.

It is also advantageous that the upper and lower faces of the body have projections for bone anchorage which extend along its walls.

According to another preferred embodiment of the invention, an implant is provided with mounting structure for mounting the anchorage reinforcement member so that it can rotate in the internal space of the body, while at the same time preventing relative translational movement between the hollow body and the anchorage reinforcement member.

The mounting structure preferably includes a cylindrical opening formed in a distal end wall of the body, and a shaft provided on the member and able to be engaged, by elastic deformation, in the opening.

In this particular embodiment, the anchorage reinforcement member preferably has the shape of a screw having two diametrically opposite flats, with the projections for bone anchorage being defined between the flats, and cutting edges being provided at the transitions between the thread of the screw and the flats in order to promote bone fusion once the implant has been put into place.

To facilitate the insertion of the implant, the distance between the opposite flats is not greater than the distance between the upper and lower faces of the body.

According to another preferred embodiment, of the invention, an implant for surgery of the spine includes an essentially hollow body which can be inserted into an intervertebral space, the body having a group of generally parallel walls defining at least two internal spaces situated side by side and exposed to the overlying and underlying vertebrae which define the intervertebral space. The implant additionally has at least two anchorage reinforcement members having, on their external surface, projections for bone anchorage having a diameter greater than the overall height of the body, the said anchorage reinforcement members being adapted to be threaded into respective internal spaces of the body.

In this particular embodiment, the anchorage reinforcement members are preferably identical. The invention furthermore proposes that the hollow body can have different geometries. In one preferred embodiment, the upper and lower surfaces of the hollow body are inclined in relation to one another, with a distance between them which decreases from the proximal end towards the distal end of the body. In another preferred embodiment, the upper and lower surfaces of the hollow body are inclined in relation to one another, with a distance between them which decreases from a first lateral side of the body towards the opposite lateral side.

The invention furthermore proposes a set of implants for forming a spinal implant intended to be inserted into an intervertebral space of the human vertebral column by being adapted to the geometry of the intervertebral space. This set of implants includes a plurality of hollow bodies, each having a pair of lateral walls defining an internal space and each able to be inserted into an intervertebral space in such a way that the internal space is exposed to the overlying and underlying vertebrae which define the intervertebral space. Each of the hollow bodies preferably has a specific size and shape, at least one anchorage reinforcement member having, on its external surface, projections for bone anchorage having a diameter greater than the overall height of the bodies. The anchorage reinforcement member is able to be driven in rotation in the internal space of any one of the bodies, in such a way that a specific hollow body appropriate to the particular configuration of a given intervertebral space can be chosen from among the plurality of hollow bodies.

The specific sizes and shapes of the bodies may vary. Certain preferred bodies have different angles of inclination between their upper and lower surfaces. Other preferred bodies have different widths. The widest hollow bodies preferably have lateral walls in which through-openings are formed which extend between the upper and lower faces of the bodies. The hollow bodies may also have different heights and different lengths.

Regardless of their size or shape, the hollow bodies are preferably adapted to receive the same type of anchorage reinforcement member.

The invention also proposes a method for positioning, in an intervertebral space of a human vertebral column, an implant including an essentially hollow body having a pair of lateral walls enclosing an internal space, and an anchorage reinforcement member having, on its external surface, projections for bone anchorage having a diameter greater than the overall height of the body, and adapted to be driven in rotation in the internal space of the body. The method preferably includes selecting a hollow body from a set of hollow bodies having different shapes and dimensions. The selected hollow body is preferably adapted to fit with the configuration of the intervertebral space. The method also includes filling the selected hollow body with a substance which promotes bone growth, pushing the hollow body into the intervertebral space in such a way that the internal space thereof is exposed to the overlying and underlying vertebrae which define the intervertebral space, and inserting the anchorage reinforcement member into the hollow body in such a way that the projections of the bone anchorage member anchor in the overlying and underlying vertebrae.

In embodiments where the intention is to position an implant whose body has lateral walls provided with through-openings extending between the upper and lower faces of the body, the method can additionally include, before the step of pushing the hollow body into the intervertebral space, a step in which the through-openings are filled with a substance which promotes bone growth.

BRIEF DESCRIPTION OF THE DRAWINGS

Other aspects, aims and advantages of the present invention will become more apparent on reading the following detailed description of preferred embodiments thereof, given by way of example, and with reference being made to the attached drawings, in which:

FIG. 24 is an exploded perspective view of an implant according to a fifth embodiment of the invention.

DETAILED DESCRIPTION

Figure 1:
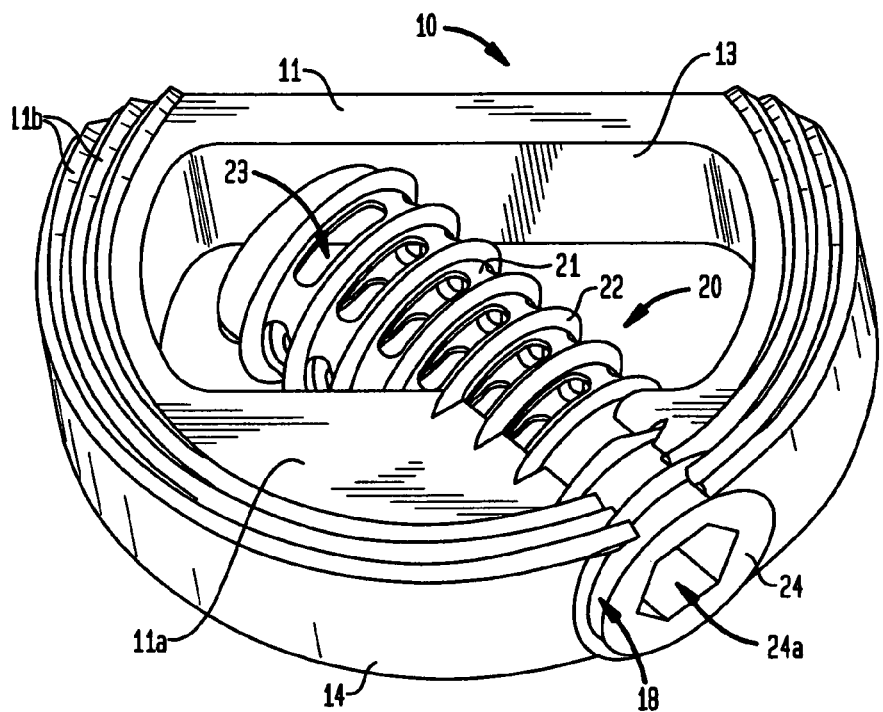
FIG. 1 is a perspective view of an implant according to a first embodiment of the invention.
Figure 2:
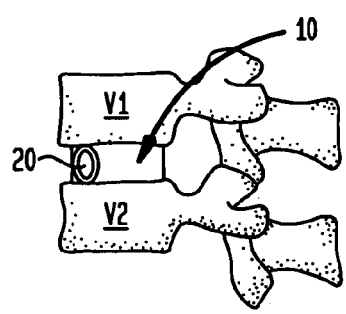
FIG. 2 is a side view of the implant of FIG. 1 placed between two vertebral plates.

Where possible, identical or similar elements or parts are designated by the same reference labels.

The terms "proximal" and "distal" used throughout the present description correspond, respectively, to that end of the implant nearest the surgeon during a fitting operation and the end of the implant furthest from the surgeon.

Referring to FIGS. 1-8, a cage-type intersomatic implant is shown which is made up of two parts, namely a body 10 and an anchorage reinforcement member 20.

The body 10 has the general shape of a ring, with an upper face 11, a lower face 12, an inner face 13 and an outer face 14.

The contour of the body 10 has a circular shape truncated by a part of rectilinear contour, its width being equal, for example, to about four-thirds of its depth.

Along the rectilinear contour part, on the upper and lower faces 11 and 12, roughened areas are formed to ensure that the implant is immobilized relative to the overlying V1 and underlying V2 vertebral plateaus or plates (see FIG. 2) when the implant is compressed between these.

The roughened areas are in the form of three upper ribs 11b and three lower ribs 12b, of triangular cross-section and of circular trajectories concentric with the circular contour part of the body.

Opposite the rectilinear contour part, the body has a thicker wall, produced by an upper land and a lower land.

Formed in this wall part there is a tapped-through orifice 18 whose axis extends obliquely, and preferably at about 45°, relative to the vertical plane perpendicular to the plane distal wall of the implant, which vertical plane corresponds to the sagittal plane.

In addition, the axis of this orifice 18, which extends essentially horizontally, passes substantially through the center of the circular contour part, going towards the opposite region situated at the transition between the circular contour part and the rectilinear contour part.

The implant according to the invention additionally includes the anchorage reinforcement member 20 adapted to reinforce the anchoring on the vertebral plateaus.

In the embodiment shown in FIGS. 1-8, the member 20 includes a hollow cylindrical core 21 having a helical thread 22 on the outer surface thereof that is threadable into the internal thread formed in the orifice 18.

Formed between the adjacent thread sections there are a plurality of openings 23, oblong in the direction of the helical run of the thread, for reasons explained below.

At its distal end, the member 20 is closed by a solid wall 25. At its proximal end, the member 20 includes a solid part 24 in which there is formed a hollow recess 24a, for example of hexagonal cross-section, for introduction of a screwing instrument (not shown).

Figure 3:
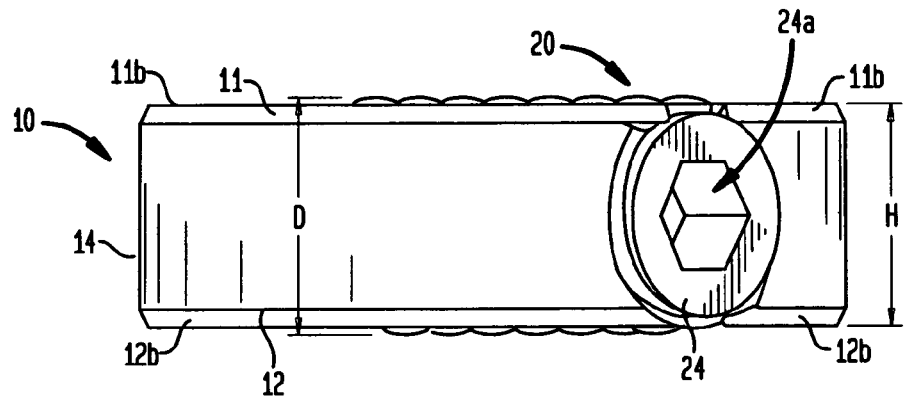
FIG. 3 is a front view of the implant of FIG. 1.
Figure 4:
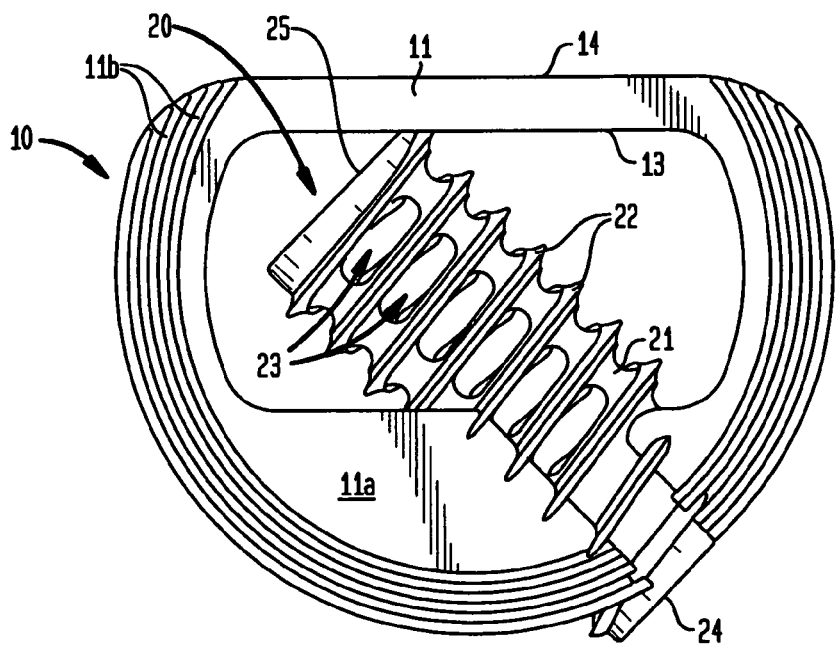
FIG. 4 is a plan view of the implant of FIGS. 1 and 3.
Figure 5:
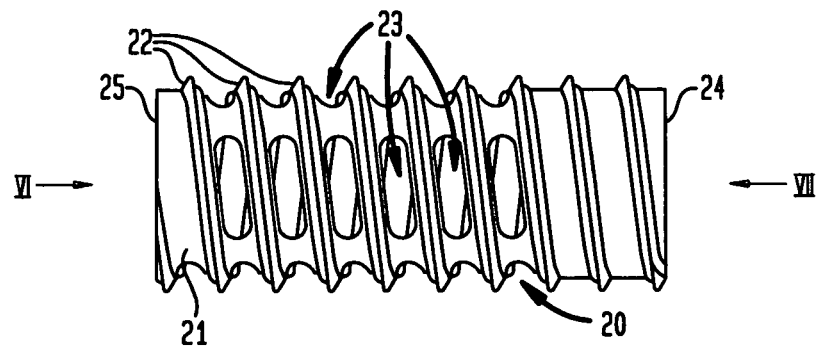
FIG. 5 is a side view of an element of the implant of FIG. 1.
Figure 6:
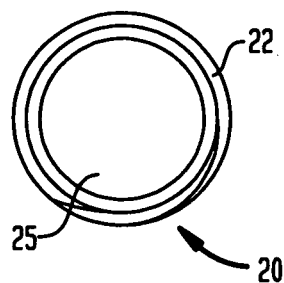
FIG. 6 is an end view in the direction of arrow VI in FIG. 5.
Figure 7:
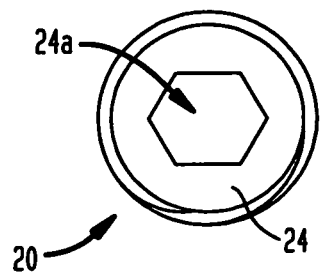
FIG. 7 is an end view in the direction of arrow VII in FIG. 5.
Figure 8:
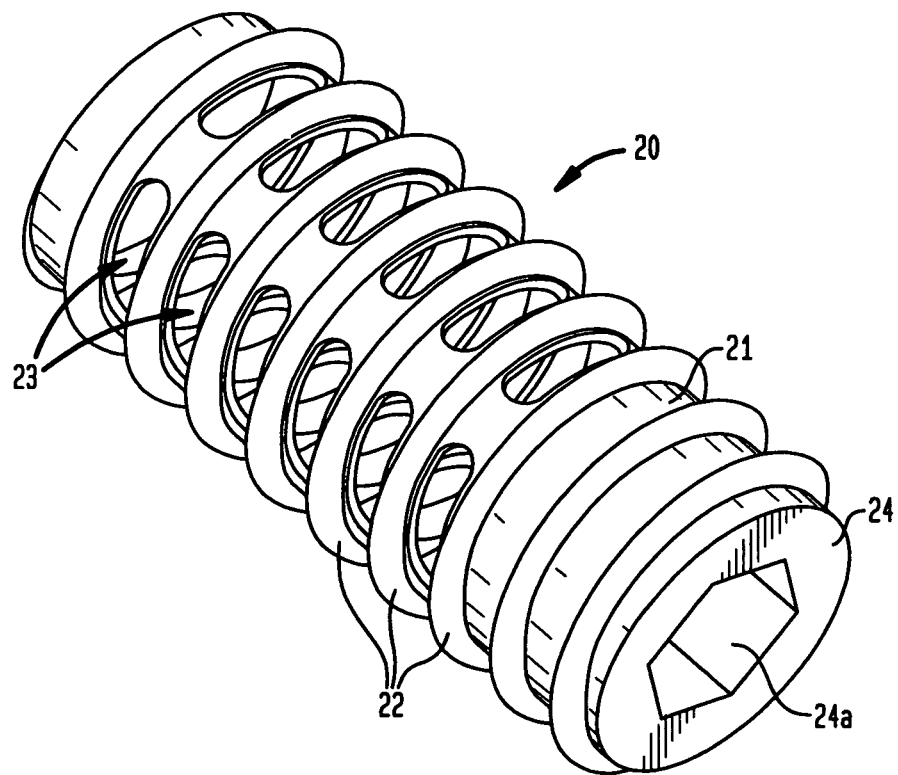
FIG. 8 is a perspective view of the element of FIGS. 5 to 7.
Figure 9:
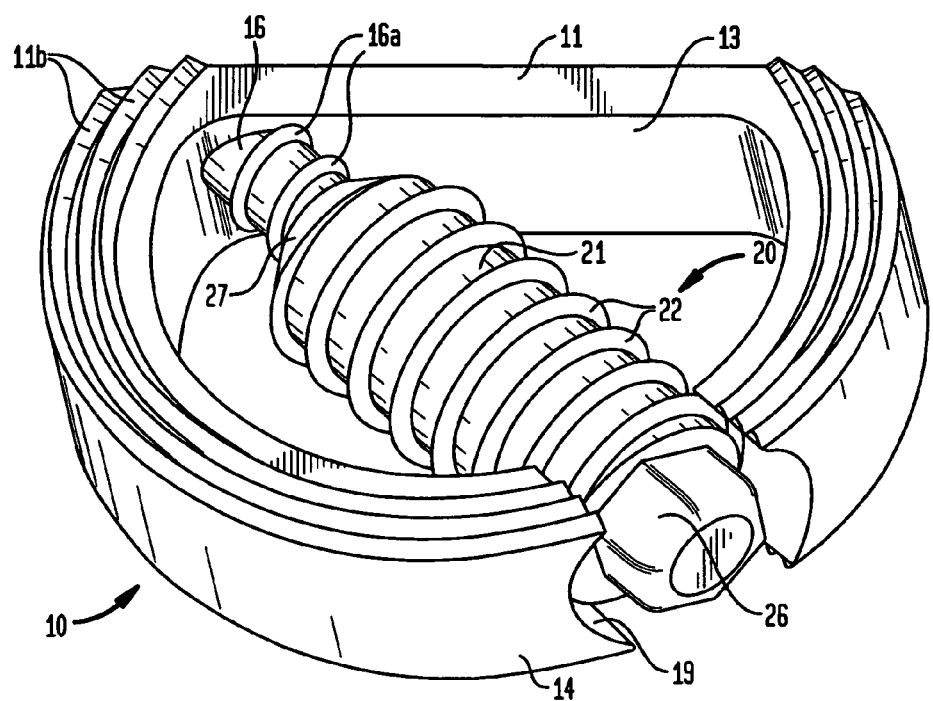
FIG. 9 is a perspective view of an implant according to a second embodiment of the invention.
Figure 10:
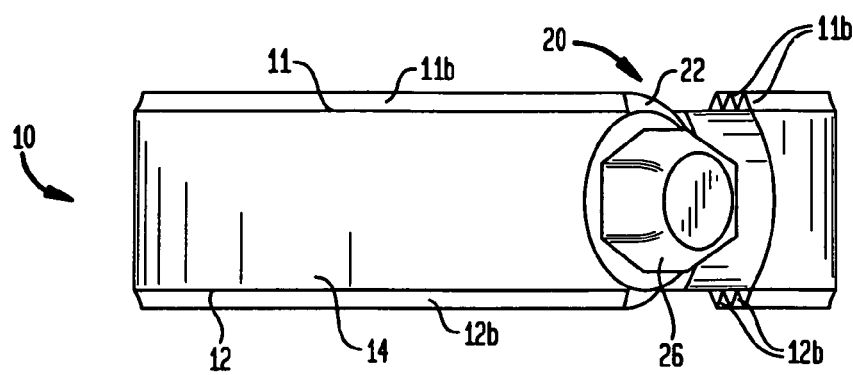
FIG. 10 is a front view of the implant of FIG. 9.
Figure 11:
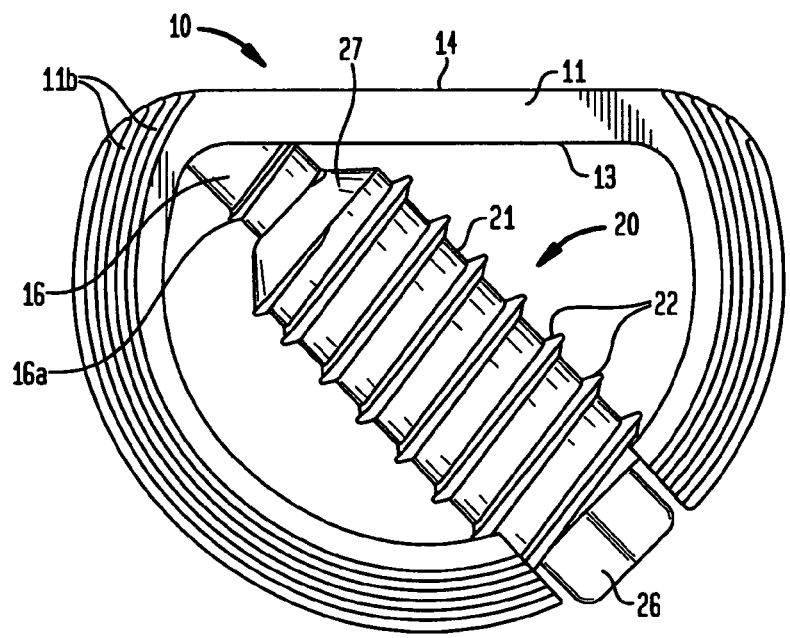
FIG. 11 is a plan view of the implant of FIGS. 9 and 10.
Figure 12:
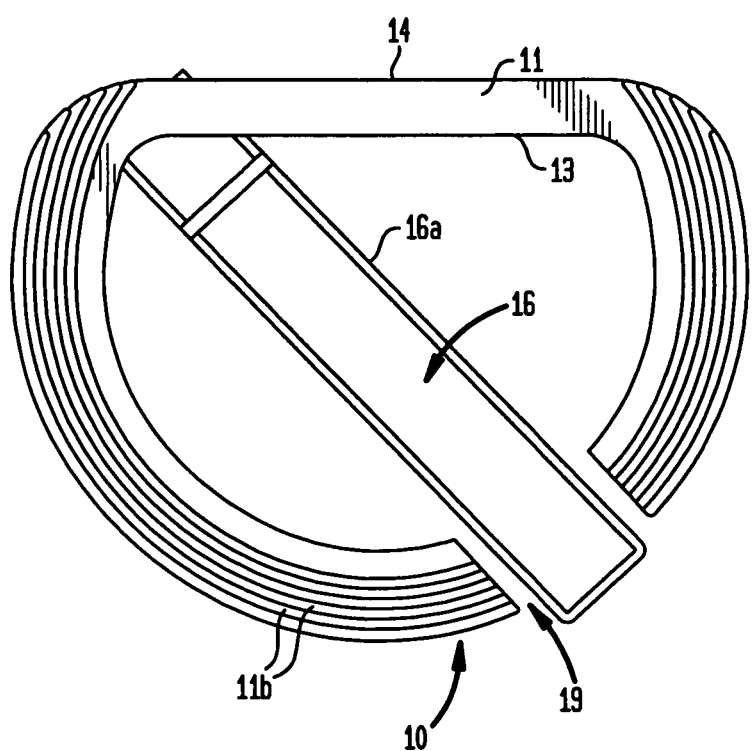
FIG. 12 is a plan view of a first element of the implant of FIGS. 9 to 11.
Figure 13:
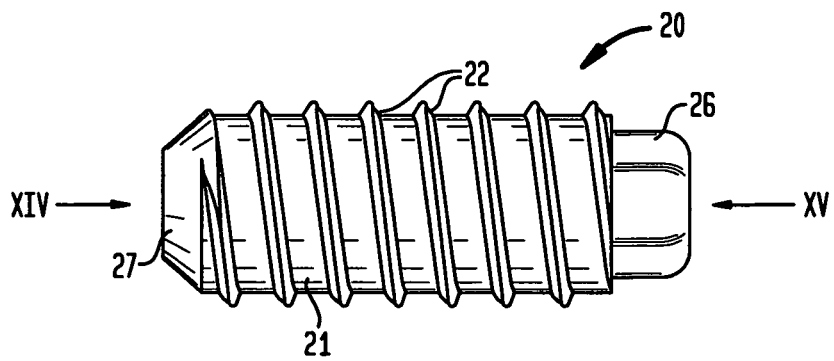
FIG. 13 is a side view of a second element of the implant of FIGS. 9 to 11.
Figure 14:
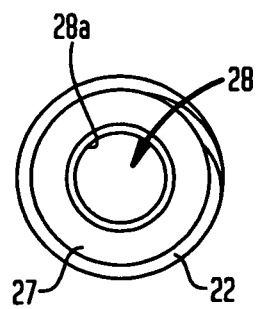
FIG. 14 is an end view in the direction of arrow XIV in FIG. 13.
Figure 15:
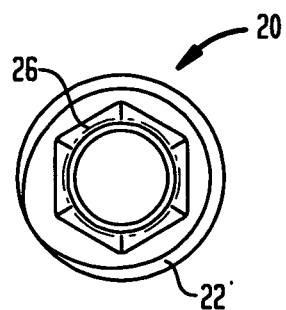
FIG. 15 is an end view in the direction of arrow XV in FIG. 13.

It is important to note, as is shown in particular in FIG. 3, that the overall diameter D within which the thread 22 of the member 20 is inscribed is slightly greater than the overall height H within which the body 10 is inscribed, for reasons which are explained below.

The length of the member 20 is such that it can be screwed into the orifice 18 of the body 10 until the outer face of its proximal solid part 24 is substantially aligned with the outer face 14 of the body 10 adjoining the orifice.

In certain preferred embodiments, the implant is positioned between vertebrae after the vertebrae have been distracted and a portion of the intervertebral disc has been removed. The body 10 of the implant, without its member 20, is put into the disc space, by an anterior or posterior approach. The internal space of the body is preferably first filled with bone graft material in order to ensure eventual intervertebral fusion by osteogenesis.

The contour of the body 10, with the flat in the proximal part, is such that it is easily inscribed within the surface area of a vertebral plateau. If necessary, it is possible to offer the surgeon bodies 10 having different sizes, the particular size being selected as a function of the spinal anatomy of the patient, as will be seen in greater detail below.

The two vertebrae are then released, and an initial immobilization of the body between the vertebral plateaus V1 and V2 is ensured with the aid of the ribs 11b, 12b.

The member 20 is then screwed into the orifice 18 with the aid of an instrument. During this movement, the crest of the thread 22, which projects slightly upwards and downwards in relation to the crest parts of the ribs 11b, 12b, cuts into the opposing faces of the overlying and underlying vertebral plateaus in the manner of a self-tapping screw, and thus affords a supplementary anchoring which will firmly immobilize the implant relative to these plateaus.

In addition, the rotation of the member 20 as it penetrates the internal space of the body 10 ensures that some of the bone graft material packed in the internal space will migrate through the openings 23 and into the internal space of the hollow member 20. As a result, bone growth will also be obtained through the member 20, and this will advantageously immobilize the member 20 in terms of any rotation, particularly reverse rotation, that risks affecting the stability of the implant in the long term. Alternatively, it is also possible for the member 20 to be filled beforehand with bone graft material.

FIGS. 9 to 15 illustrate a second embodiment of the present invention.

In these figures, elements or parts which are identical or similar to those in FIGS. 1 to 8 are designated by the same reference labels, and only the differences between this second embodiment and the first will be described.

It will first be noted that the body 10, which has the same contour as in the case of FIGS. 1 to 8, has a wall of essentially constant thickness over its whole periphery.

Instead of the tapped-through orifice 18 in the first embodiment, this body includes a smooth-through orifice 19.

Moreover, a cylindrical rod 16 provided with a thread 16a extends along the axis of the orifice 19 starting from the opposite region of the body 10, situated essentially at the transition between its circular contour and straight contour parts.

In addition, the member 20, which has substantially the same external contour as in the case of the first embodiment, is solid, except for a central bore 28 which opens out on its rear face and in which there is formed an internal thread 28a complementary to the thread 16a formed on the protruding rod 16 of the body.

It will be observed here that the helical pitch of the thread 16a and of the associated internal thread 28a is chosen substantially or exactly equal to the helical pitch of the thread 22 which is still present on the outer surface of the member 20.

A frustoconical part 27 is provided around the mouth of the bore 28.

The member 20 has, on its front face, a screwing arrangement which preferably includes a projecting head 26, such as a head having a hexagonal cross-section.

The implant according to this second embodiment is used essentially in the same way as that explained above.

The essential difference lies in the fact that the member 20 is screwed onto the rod 16 in the manner of a nut, the size of the orifice 19 being chosen so as not to form an obstacle to this screwing. In this respect it suffices to choose an orifice 19 with a diameter slightly greater than the overall diameter of the thread 22. The frustoconical part 27 of the member 20 makes it easier to introduce the rear end of the member into the orifice 19 prior to screwing.

As the pitch of the thread 16a is the same as that of the thread 22, the advance of the member 20 into the body 10, at the same time as the member is being driven in rotation, is such that the thread 22 here once again bites into the vertebral plateaus in the manner of a self-tapping screw.

In certain preferred embodiments, the upper and lower annular faces 11 and 12 of the body 10 extend in planes which are slightly oblique in relation to each other, so as to adapt to the shape of the intervertebral space in question. Thus, as will be seen below, the surgeon may be provided with bodies 10 having different inclinations in order to adapt to the anatomy of the vertebrae which are to be treated.

The embodiment shown in FIGS. 9 to 15 is advantageous in that the external contour of the member 20 can be given a slightly frustoconical shape in such a way that the amount by which the thread 22 projects relative to the crests of the ribs 11a and 11b remains essentially constant from the front to the rear of the implant, and because the vertebral faces concerned are substantially parallel to the upper and lower faces of the body 10, the anchoring afforded via the thread is essentially of the same magnitude from the proximal end to the distal end.

Figure 16:
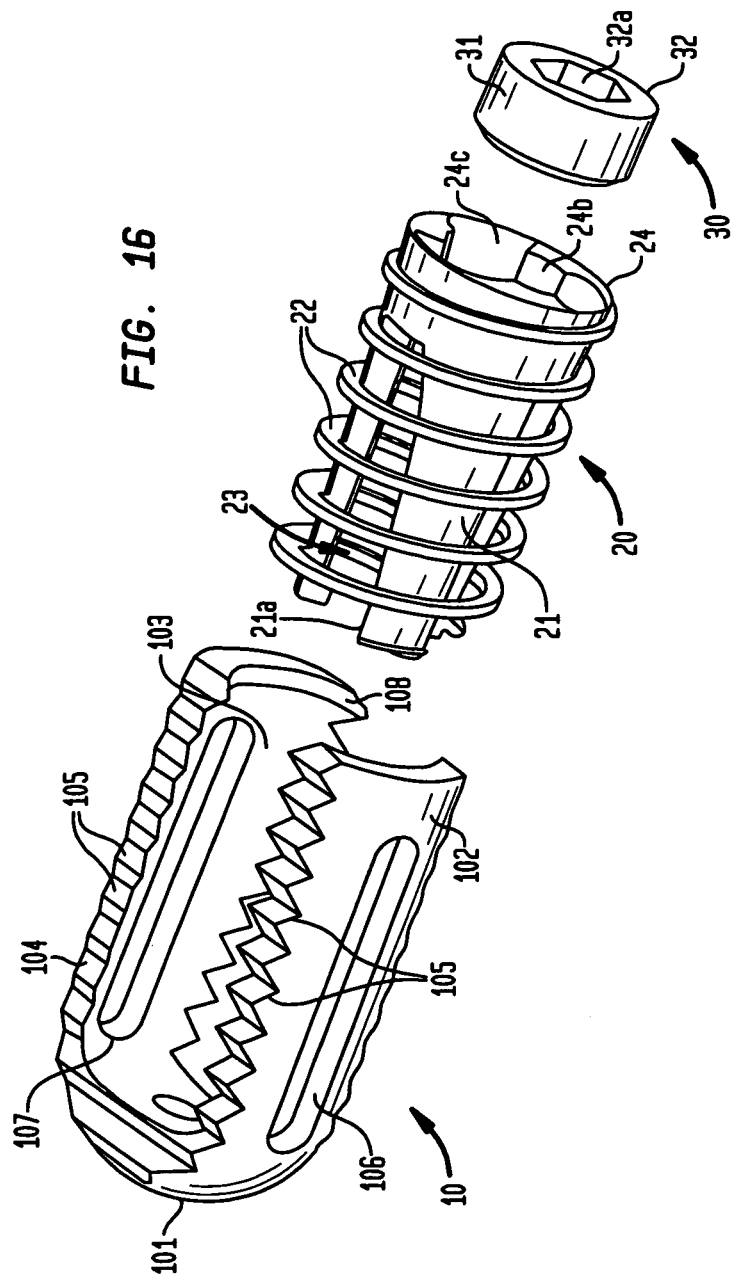
FIG. 16 is an exploded perspective view of an implant according to a third embodiment of the invention.
Figure 17:
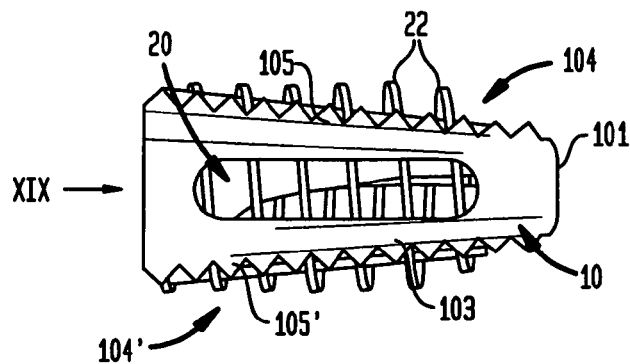
FIG. 17 is a side view of the implant of FIG. 16, when the implant is assembled.
Figure 18:
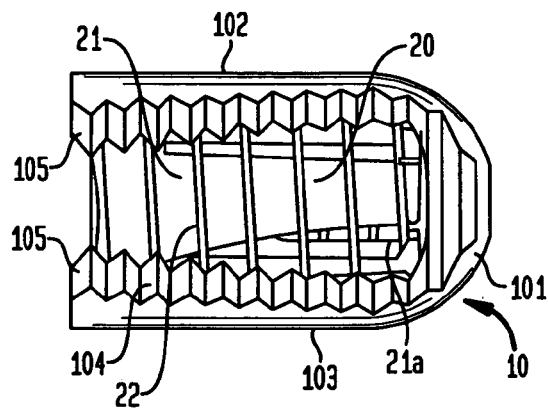
FIG. 18 is a plan view in the direction of arrow XVIII in FIG. 17.
Figure 19:
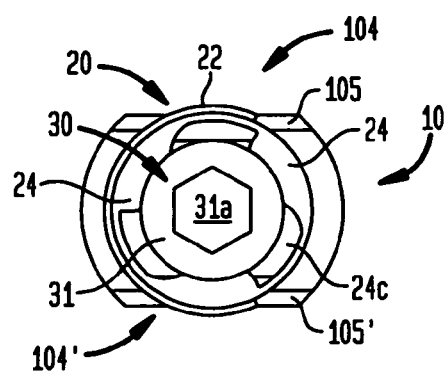
FIG. 19 is a view in the direction of arrow XIX in FIG. 17.
Figure 20:
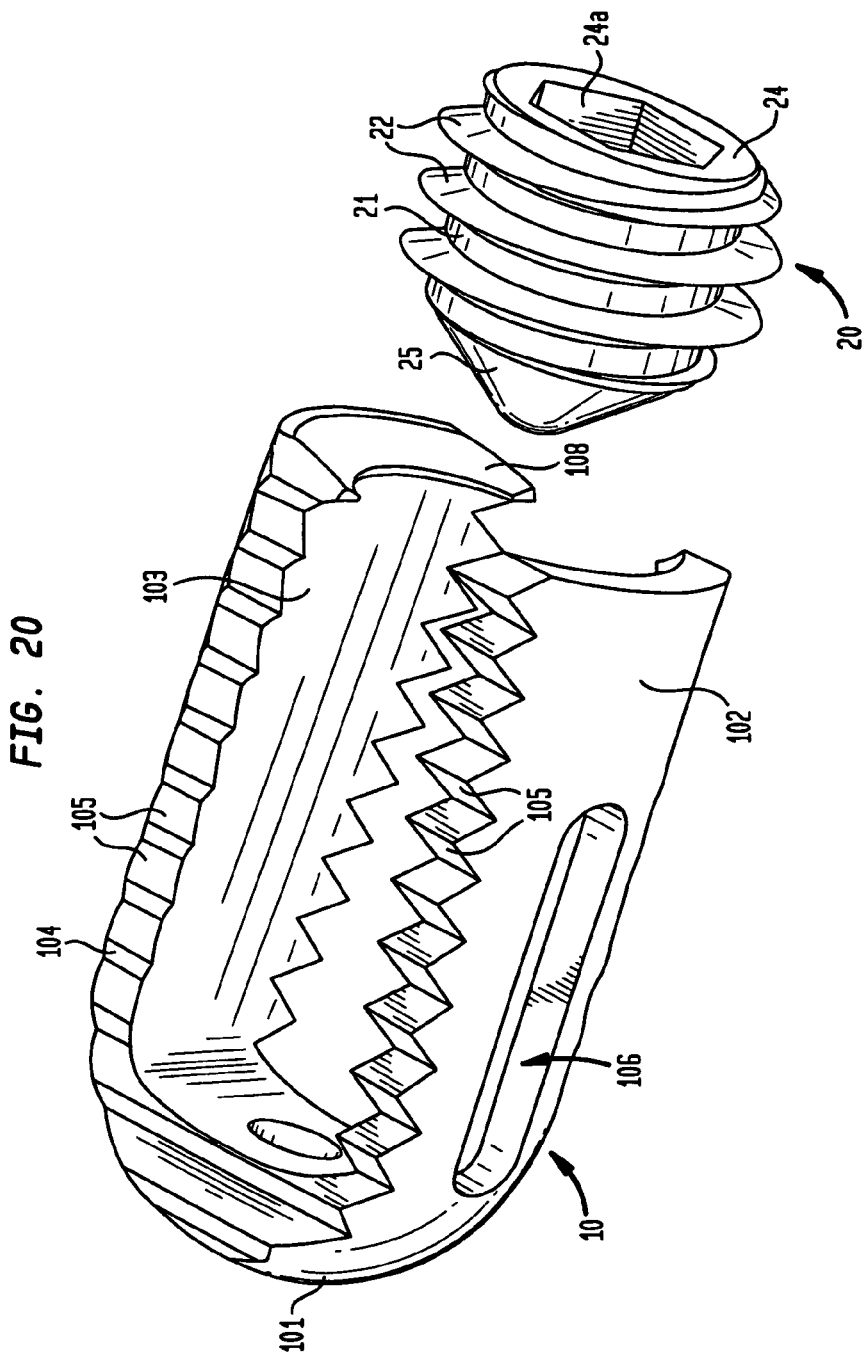
FIG. 20 is an exploded perspective view of an implant according to a fourth embodiment of the invention.
Figure 21:
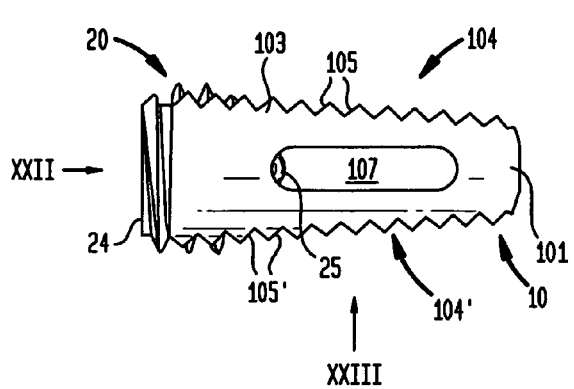
FIG. 21 is a side view of the implant of FIG. 20, when the implant is assembled.
Figure 22:
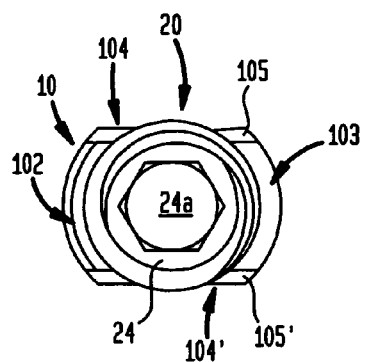
FIG. 22 is a view in the direction of arrow XXII in FIG. 21.
Figure 23:
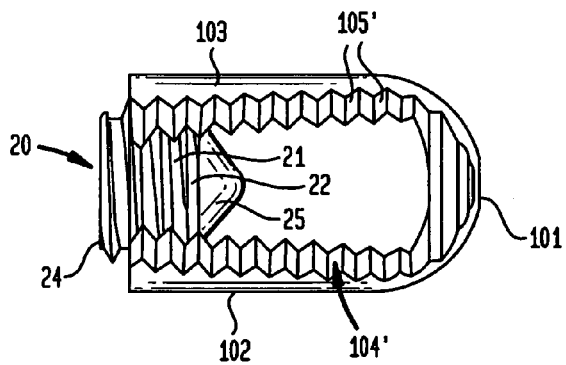
FIG. 23 is a view in the direction of arrow XXIII in FIG. 21.
Figure 26:
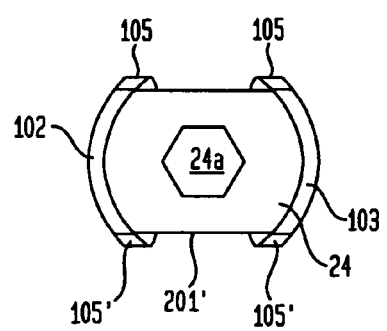
FIG. 26 is a view in the direction of arrow XXVI in FIG. 25.
Figure 25:
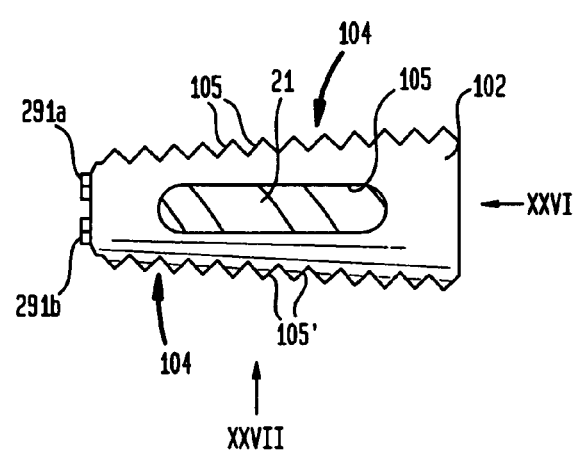
FIG. 25 is a side view of the implant of FIG. 24, when the implant is assembled.
Figure 27:
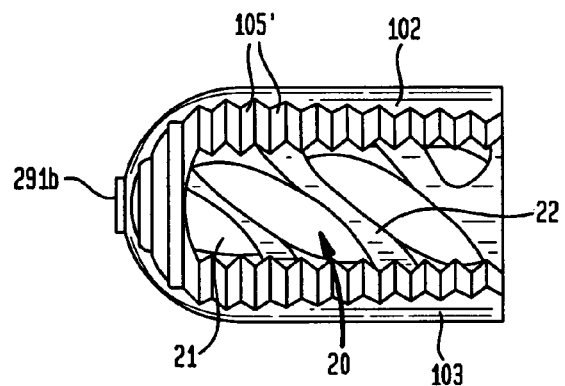
FIG. 27 is a view in the direction of arrow XXVII in FIG. 25.
Figure 28:
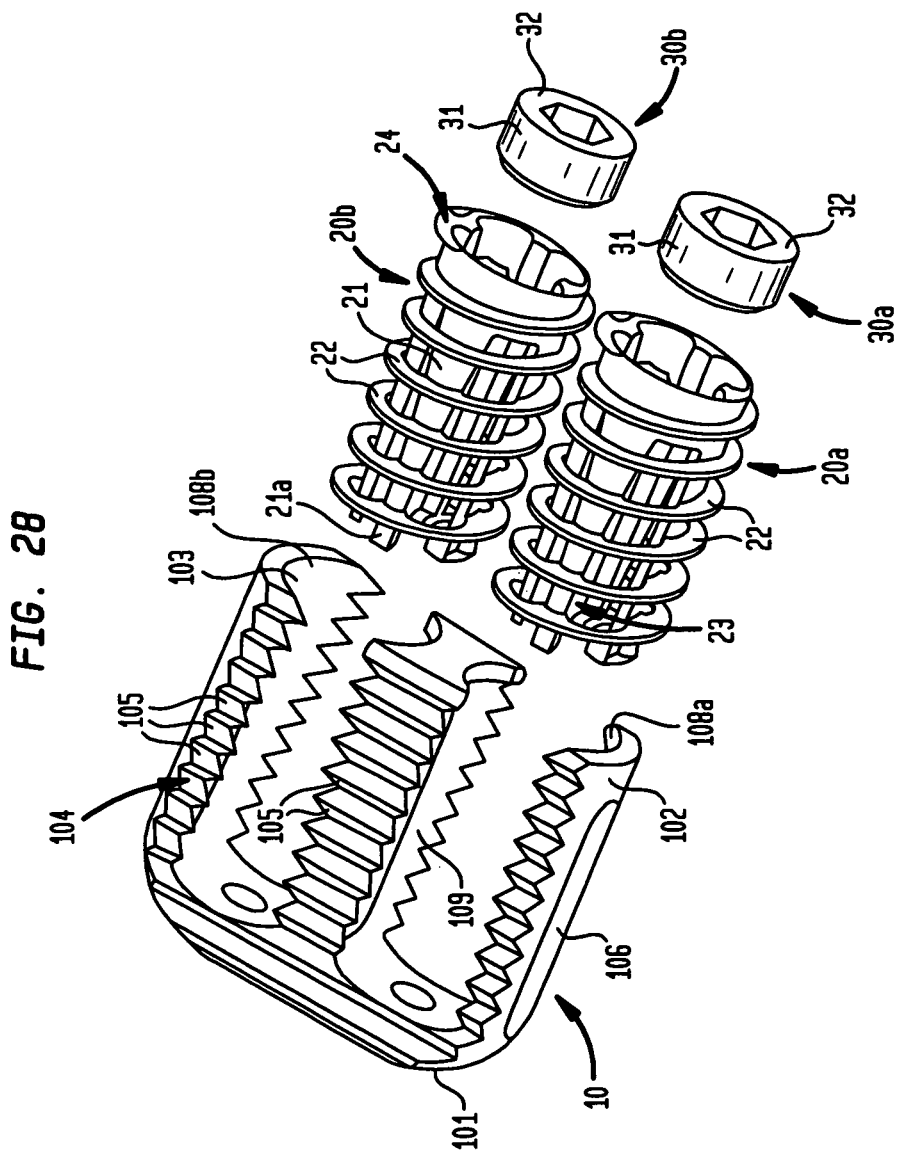
FIG. 28 is an exploded perspective view of an implant according to a variant of the third embodiment of the invention.
Figure 29:
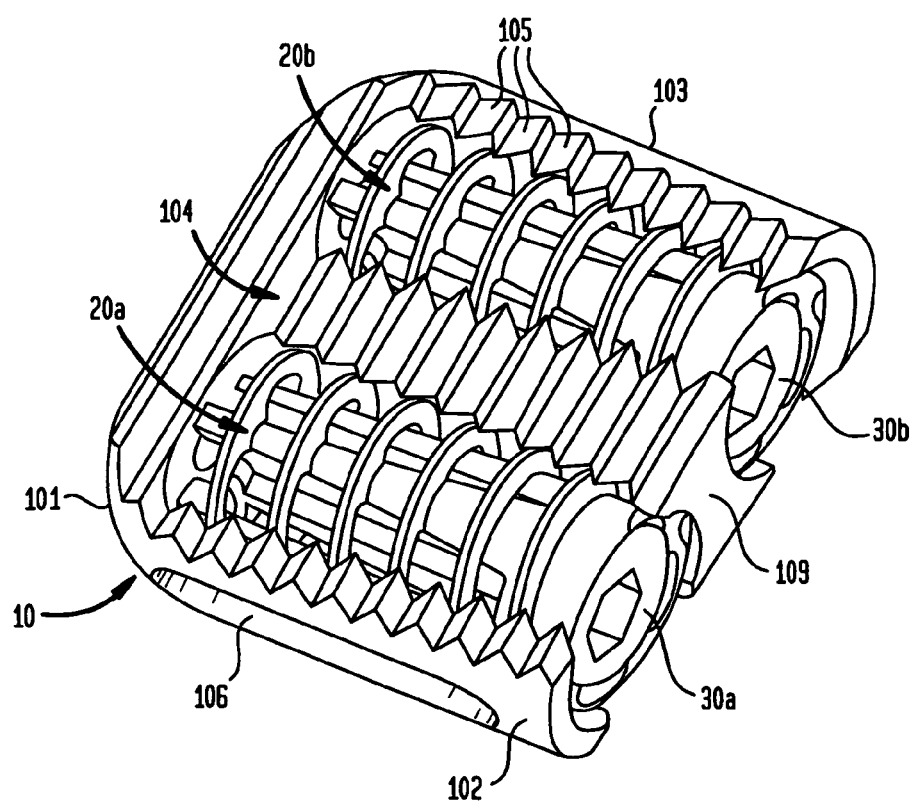
FIG. 29 is a perspective view of the implant of FIG. 28 in the assembled state.

Referring now to FIGS. 16 to 19, an implant according to another preferred embodiment includes a body 10 which, in horizontal section, has the general shape of a U, with a bottom 101, or distal wall, and two essentially parallel lateral walls or branches 102, 103. The body includes upper and lower U-shaped faces 104 and 104', respectively, on which there are formed bone anchorage teeth 105, 105', respectively. The bone anchorage teeth are sharp-edged teeth of triangular profile, which fulfill a role analogous to that of the ribs 11b in the preceding embodiments. Referring to FIG. 17, the upper and lower faces 104, 104' converge slightly towards one another from the trailing end to the leading end 10 of the hollow body.

The distal wall 101 has a tapped bore that permits temporary fixing of an instrument (not shown) for fitting the body in the intervertebral space.

The branches 102, 103 define a generally cylindrical internal space, for reasons explained below.

The two lateral branches 102, 103 of the body each include a respective longitudinal through-slot 106 and 107 for permitting lateral bone growth.

The proximal end of the body 10, remote from its distal end 101, has a generally circular opening delimited by a reentrant thread 108 provided at the proximal free ends of the two branches 102, 103.

The implant includes an anchorage reinforcement member 20 provided with a hollow core whose outer surface is slightly frustoconical, tapering from its proximal end towards its distal end. A continuous thread 22 is formed on the outer surface of the core 21.

The thread 22, in the form of a helically configured flat band, cooperates with the reentrant thread 108 of the body 10 to allow the member 20 to be screwed inside the body.

As shown in FIG. 16, the core 21 is made up of three angularly offset longitudinal branches which are separated by longitudinal empty spaces 23.

Each of the branches includes a leading edge including a cutting edge 21a. As the member 20 is rotated, the cutting edge 21a scrapes the bone material from the overlying and underlying vertebrae. In this way, screwing in the member 20 will allow the internal space of the implant to be filled with bone chips, something which will help the graft to take and which will finally fuse the two vertebrae by means of bone growth.

The external diameter of the thread 22 is preferably very similar to the internal diameter of the body 10, so that when the member 20 is being screwed in, it is guided inside the body.

The member 20 includes a proximal part 24 forming a bushing, the member 20 including an opening which is delimited by a plurality of bosses 24b separated by recessed zones 24c. The bosses 24b, which constitute the start of the branches 21 of the core, have an internal thread on their inner surface.

The implant also includes a generally cylindrical plug 30 having, on its outer surface, a thread 31 which is able to cooperate with the internal thread defined by the bosses 24b. The rear face 32 of the plug is provided with a recessed socket 32a for a screwing instrument.

When inserting the implant into a disc space, the body 10, without the member 20, is positioned between vertebrae. The member 20, without its plug 30, is filled with bone graft material via its rear opening. The plug 30 is then put into place in the rear opening to prevent the bone graft material from escaping. The member 20, provided with its plug, is then screwed into body 10 with the aid of a screwing instrument engaged in the socket 32a. During this operation, the thread 22 of the member 20 anchors in the opposing surfaces of the overlying and underlying vertebrae, possibly cutting off bone chips. In addition, the cutting edges 21a of the three branches 21 of the core of the member 20 attack the vertebrae so as to cut off chips which will complete the filling of the internal space of the member 20. As the core 21 of the member 20 advances, its frustoconical shape ensures compression of some of this bone material against the walls of the vertebrae, in order to assist the grafting.

FIGS. 20 to 23 illustrate a fourth embodiment of the invention in which the body 10 is similar to that described in FIGS. 16 to 19. In this particular embodiment, however, only branch 102 of the body is provided with a through-slot 106, while the other branch 103 does not have one. This type of body is advantageously used when two implants are placed in the same intervertebral space. In this case, the implants are arranged side by side in such a way that the respective slots of the two bodies are situated on the inside, in order to promote fusion with bone graft material placed in the region of the intervertebral space situated between the two implants.

In this preferred embodiment, the anchorage reinforcement member 20 includes a threaded plug that is substantially shorter than the body 10 in the axial direction. The member has a solid cylindrical core 21 provided with a thread 22 which is able to cooperate with the thread 103 of the body 10.

The rear face of the member 20 has a recessed socket 24a for a screwing instrument, and its front face 25 includes a cone with a rounded apex.

The implant according to this embodiment is intended to be used when the body 10 is filled relatively densely with bone grafts. As the member 20 is being screwed into the body 10, in addition to reinforcing the anchorage obtained with the aid of the thread 22, the member compresses the bone grafts situated in the body 10 so as to stress these bone grafts in particular in the direction of the overlying and underlying vertebral plateaus and for improving fusion.

FIGS. 24 to 27 illustrate a fifth embodiment of the invention. The body 10 of the implant has a cylindrical through-opening 101a at the distal end 101 that is arranged on the axis of the body. The proximal end of the body has an opening that is not threaded.

The anchorage reinforcement member 20 is a screw having a wide thread. At its front end the screw, has a shaft-like extension made up of two essentially semicylindrical axial lugs 29a, 29b which, at their respective free ends, have an added thickness 291a, 291b.

The two lugs 29a, 29b have an external diameter which is slightly smaller than the diameter of the opening 101a of the body 10. The lugs are also thinner so that their elastic deformability allows the member 20 to be snapped into the body 10 before it is fitted by the surgeon. Thus, the member 20 is immobilized against translation, but is free in rotation. The member 20 is guided, on the one hand, by the opening 101a and on the other hand, by the inner faces of the two branches 102, 103 of the body 10.

Another important feature of the embodiment shown in FIG. 24 is that the member 20 is delimited by two flats 201, 201', respectively, which confer upon the member a thickness which is substantially equal to the thickness of the body 10, all along the length of the body 10.

The threads form a sharp angle at the transition between the thread 22 (of square cross-section) and the flats 201, 201'.

Furthermore, as in some of the preceding embodiments, the proximal part 24 of the member 20 is provided with a recessed socket 24a for a screwing instrument.

The surgeon fits the implant in place using the following procedure. The complete implant, that is to say the body 10 enclosing the member 20 which has first been clipped on, and which has been given the angular orientation in FIG. 24, is engaged by impaction into the intervertebral space. This operation is facilitated by the fact that the member 20 does not protrude beyond the limits of the body 10. The member 20 is turned about its axis with the aid of an appropriate instrument engaged in the socket 24a, so that the sharp edges of the threads 22 attack the bone material of the overlying and underlying vertebral plateaus, in this way tearing off bone chips that will fill the free spaces existing between the body 10 and the member 20, so as to contribute to the bone fusion.

Because the member 20 is immobilized against any translation relative to the body 10, and cannot therefore be screwed into the latter or into the vertebral plateaus, the threads 22 are advantageously given a wide helical pitch so that the screwing action favors a reciprocal sliding of the threads 22 relative to the vertebral plateaus, without inducing an axial force sufficient to displace the implant in this direction.

Referring to FIGS. 28 to 32, in another preferred embodiment of the present invention, an implant includes a wide body 10 that is designed to receive two anchorage reinforcement members, 20a and 20b, respectively. To this end, the body 10 is widened and has two lateral branches 102 and 103 as well as an intermediate middle branch 109 extending between the branches 102 and 103.

The branches 102 and 109 define a first seat for the member 20a, while the branches 103 and 109 define a second seat for the member 20b. The axes of the two seats are mutually parallel, but being able, if appropriate, to adopt a certain inclination. These two seats preferably have the same configuration as the single seat of the third embodiment, and the members 20a and 20b are preferably similar to the member 20 of this same embodiment.

The body 10 is provided with bone anchorage teeth 105, 105'.

Figure 30:
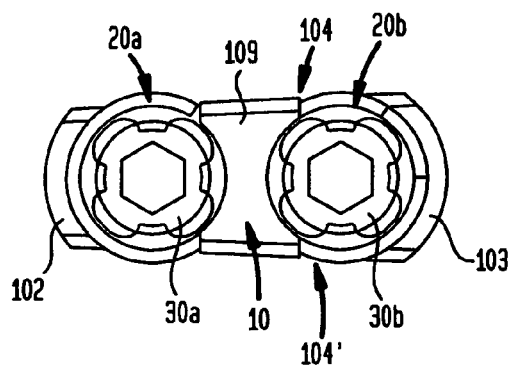
FIG. 30 is a view of the rear of the implant of FIG. 29.
Figure 31:
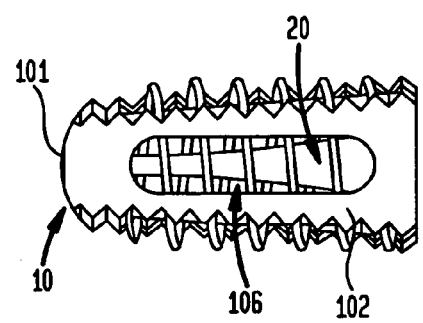
FIG. 31 is a side view of the implant of FIG. 29.
Figure 32:
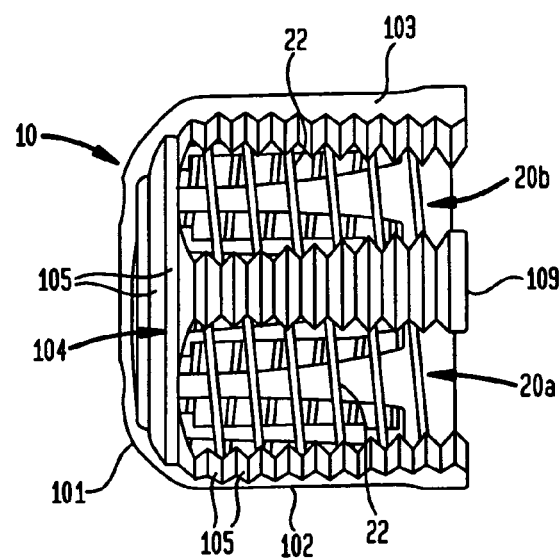
FIG. 32 is a plan view of the implant of FIG. 29.

As shown particularly in FIGS. 30 and 31, the upper and lower faces 104 and 104' of the body 10 have a dual inclination, one corresponding to the faces coming closer together in the direction towards the distal ends of the seats, and the other corresponding to the faces coming closer together in a lateral direction (from right to left in FIG. 30). An opposite inclination can be obtained by turning the body 10 around.

This dual inclination allows the body 10 to be implanted at a slant while re-establishing the lumbar lordosis in the sagittal plane.

Furthermore, the increased width of the implant ensures a more stable support between the two vertebral plateaus, while the presence of two anchorage reinforcement members 20a and 20b reinforces the resistance to slipping relative to these plateaus.

As is evident to one skilled in the art, this variant of the invention can be applied to all the other implants described in the present document, with a simple adaptation of the body 10.

Referring now to FIGS. 33 to 44, a description will be given of another variant of the implant which was described with reference to FIGS. 16 to 19.

According to this variant, the outer body 10 of the implant comprises, in the same way as before, a general U shape with two lateral branches 102 and 103 connected via a distal end wall 101, with rounded transitions.

To increase the width of the implant, and hence to improve its stability, the lateral branches 102 and 103 have, in the lateral direction, a thickness which is substantially greater than that of the branches 102 and 103 described with reference to FIGS. 16 to 19.

This thickness is preferably chosen in such a way as to give the overall width of the implant a value which is, for example, equal to about 1.5 to 2.5 times the diameter of the anchorage reinforcement member 20.

In addition, to further improve the bone fusion between the overlying and underlying vertebral plateaus, oblong through-openings 110 and 111 are provided which extend, for example, vertically between the upper face 104 and the lower face 104' of the body, in such a way that the lateral branches 102 and 103 each have a double wall. Also formed in each of these walls are generally horizontal oblong openings 106, 106', and 107, 107', respectively, which allow the internal space of the body 10 to open laterally to the outside of the body, by passing through the two double walls and the through-openings 110, 111, respectively.

Figure 43:
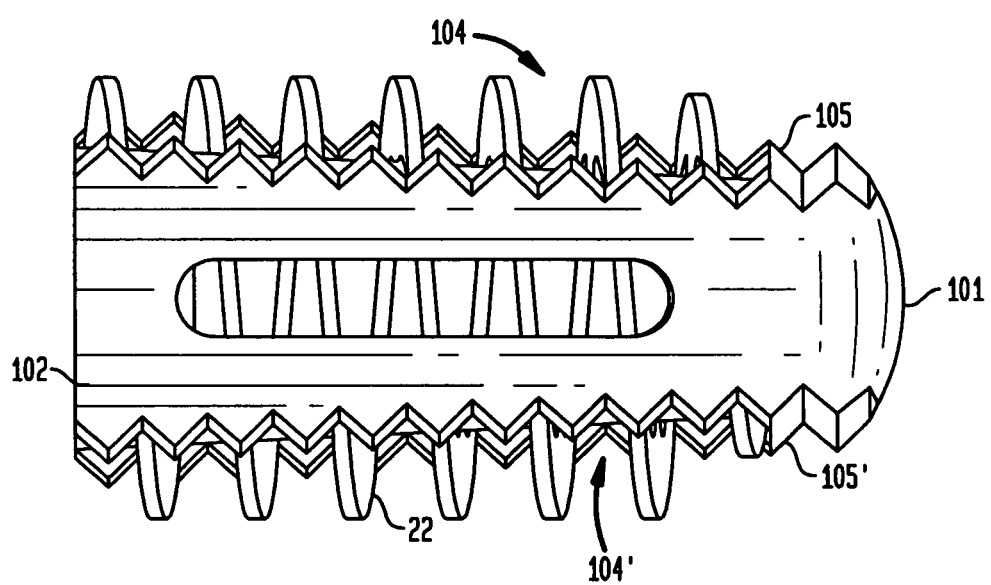
FIG. 43 is a side elevational view of the implant of FIG. 40.
Figure 44:
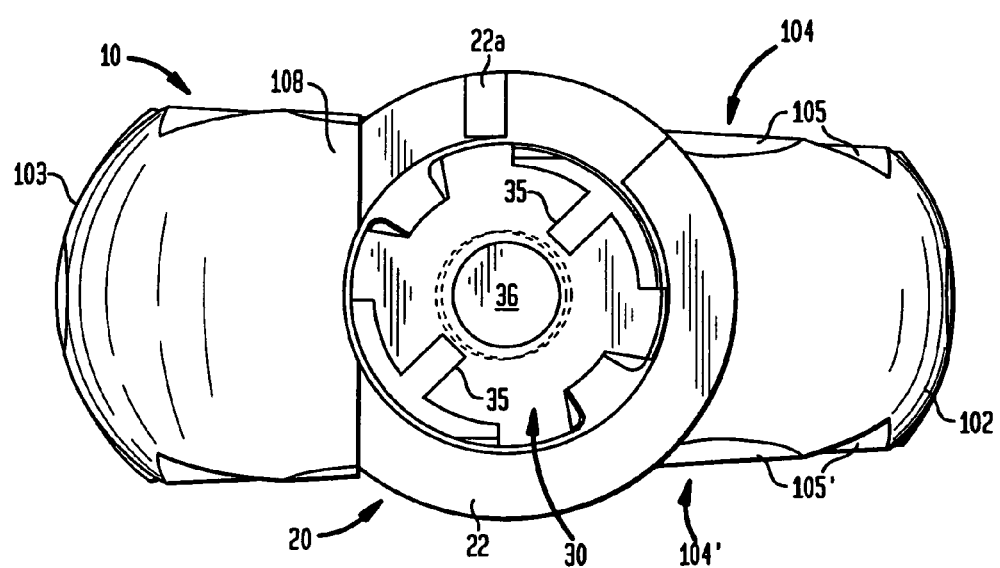
FIG. 44 is an end view, from the proximal direction, of the implant of FIG. 40.

Referring to FIGS. 43 and 44, the upper and lower faces 104 and 104' of the body have a dual inclination relative to each other, in the lateral direction and from the proximal end towards the distal end.

The anchorage reinforcement member 20 has a construction similar to that which was described with reference to FIGS. 16 to 19. It has an internal fork having two branches 21 and a helical band 22 forming a bone anchorage thread attached to the branches. The parts 21 and 22 are preferably made in one piece.

The thread 22 is preferably a self-tapping thread, which makes it possible to screw directly into the overlying and underlying vertebral plateaus without having to form a tapping in these vertebral plateaus prior to fitting. To this end, the thread 22 has, in its distal end region, a radial section 22b in the form of an outwardly turned point, and this section varies progressively, for example by about a fraction of a turn, up to a rectangular radial section 22c. In addition, the diameter of the thread 22 increases progressively from its distal end up to the part of rectangular section, which is here of constant diameter.

The outer faces of the branches 21 are tapered, the diameter decreasing from the proximal end towards the distal end.

The two branches are joined at the area of a bushing 24 which is in the form of a cylindrical ring, formed preferably in one piece with the branches.

A plug 30 having a series of flexible locking tabs 33, e.g. two pairs of tabs, can be mounted in this bushing 24 by being clipped in elastically from the outside. The tabs engage in the central opening of the bushing 24, and the ends of which tabs, in the form of teeth 33a, can catch onto the internal edge of the bushing 24.

The member 20 and its plug 30 are made integral in terms of rotation by means of the fact that each pair of tabs 33 tightly encloses the start of a respective branch 21 of the fork.

The plug 30 also has a centrally arranged tapped bore 34 adapted to receive a threaded rod-shaped end of an instrument (not shown) for fitting the member 20.

Figure 40:
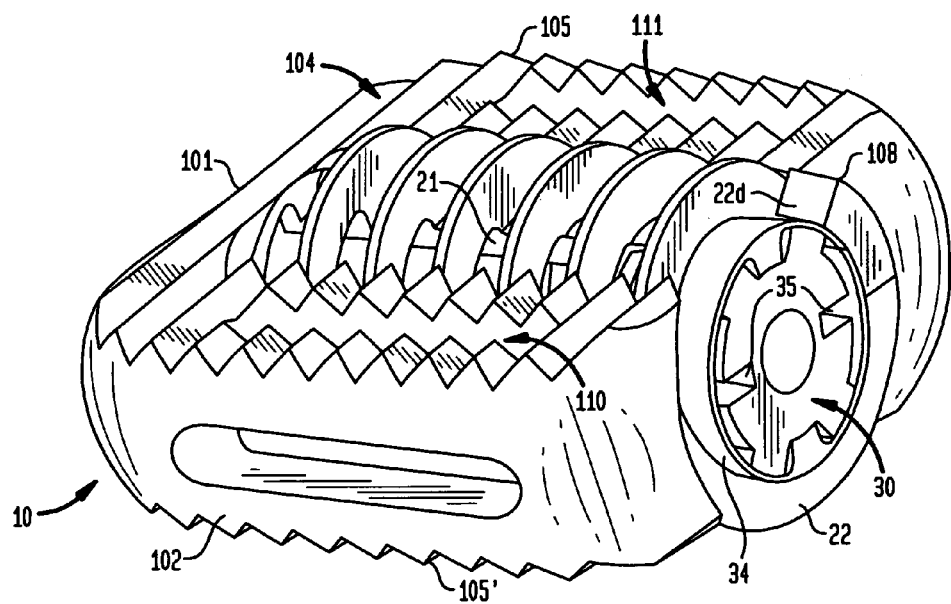
FIGS. 40 and 41 show two perspective views of the implant of FIG. 33 in the assembled state.
Figure 41:
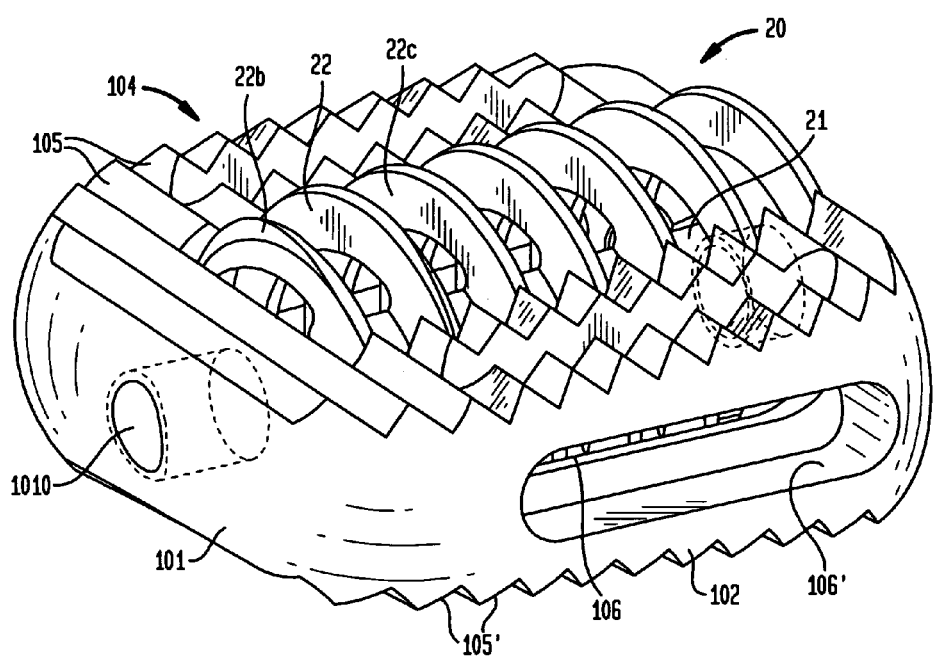
Figure 42:
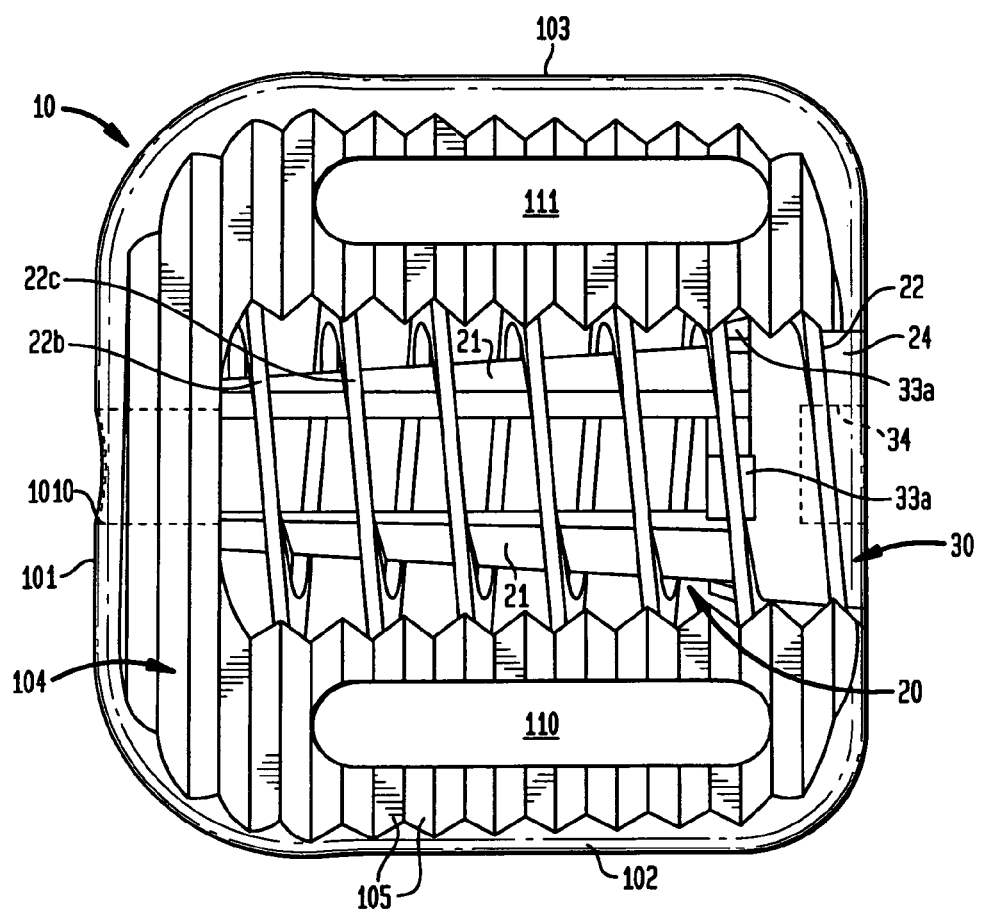
FIG. 42 is a plan view of the implant of FIG. 40.

Referring to FIGS. 40 and 44, two diametrically opposite notches 35 are formed on either side of the tapped bore 34, to permit angular indexing of the above mentioned instrument, in this case equipped with complementary arrangements, relative to the plug 30 and, thus, to the whole of the anchorage reinforcement member 20.

Referring to FIG. 44, the thread 108 permitting screwing cooperation between the outer body 10 and the member 20 is provided only on one of the lateral branches of the body, in the form of a reentrant flange ending in a generally rectilinear edge 108a.

Figure 33:
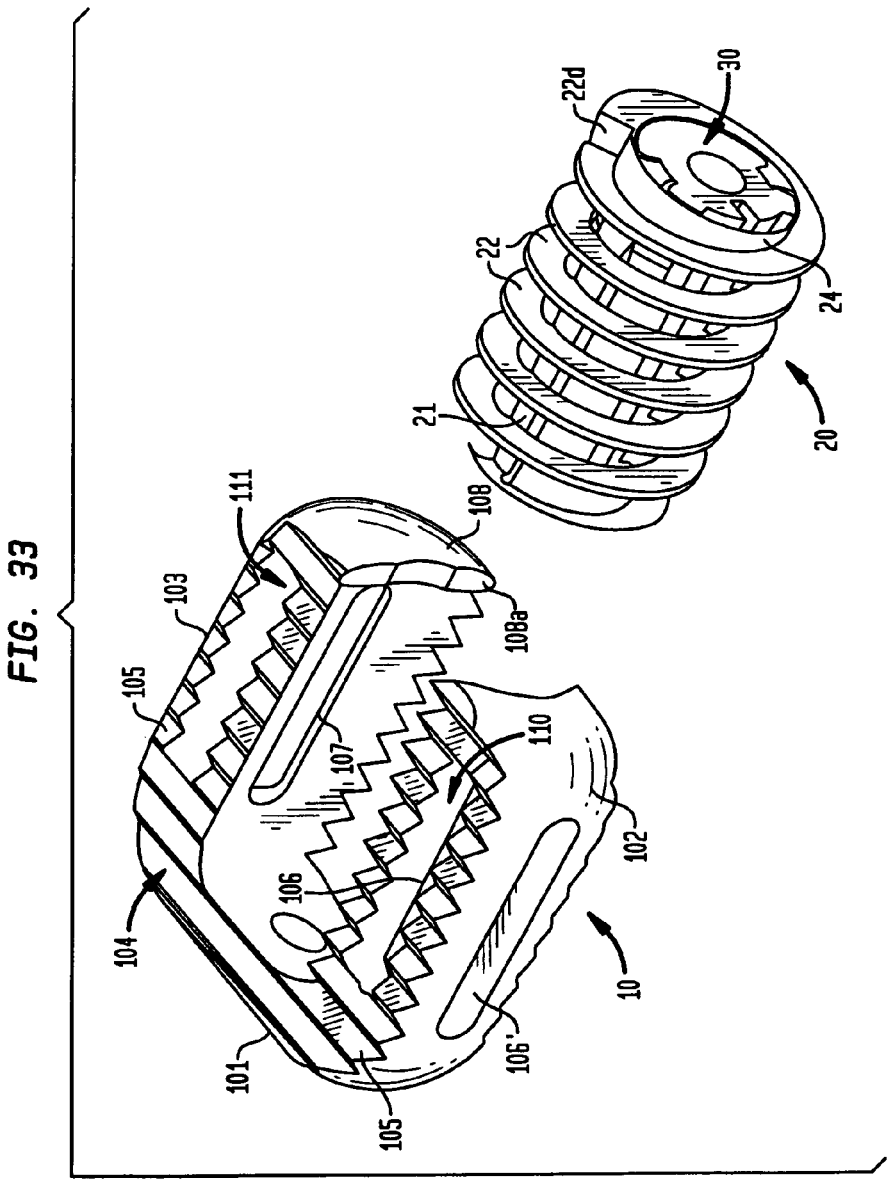
FIG. 33 is a perspective view, before assembly, of an alternative design of the third embodiment of the invention.
Figure 34:
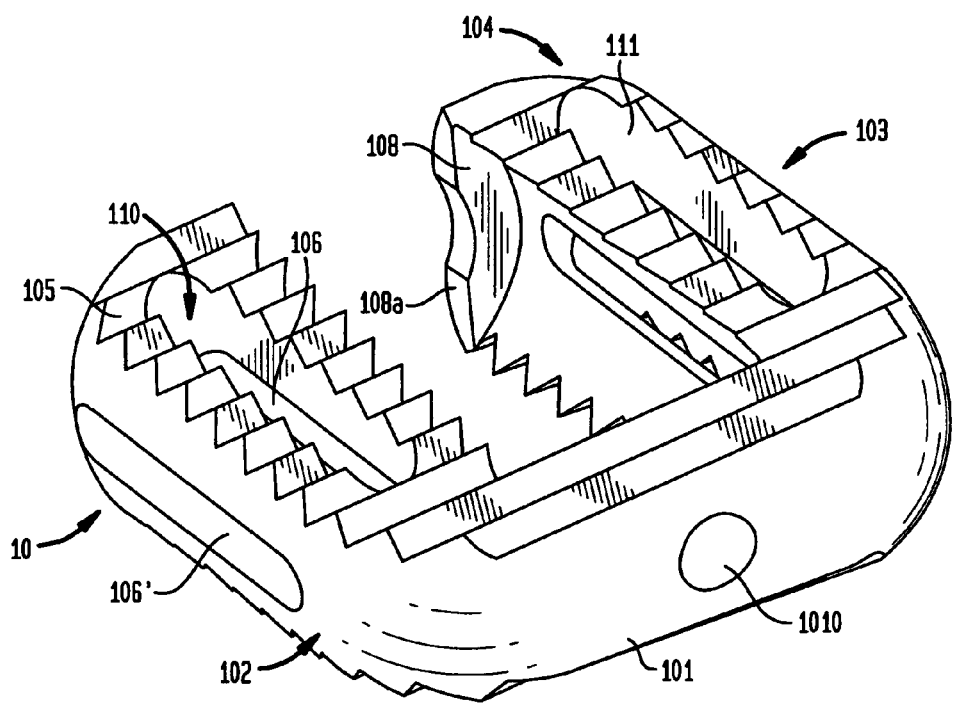
FIGS. 34 to 36 are three perspective views of the body of the alternative design shown in FIG. 33.
Figure 35:
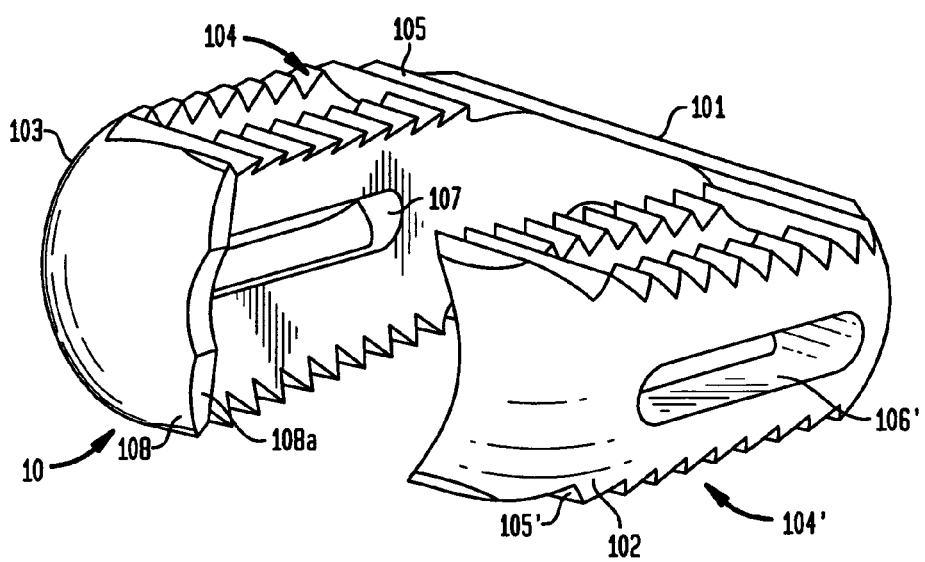
Figure 36:
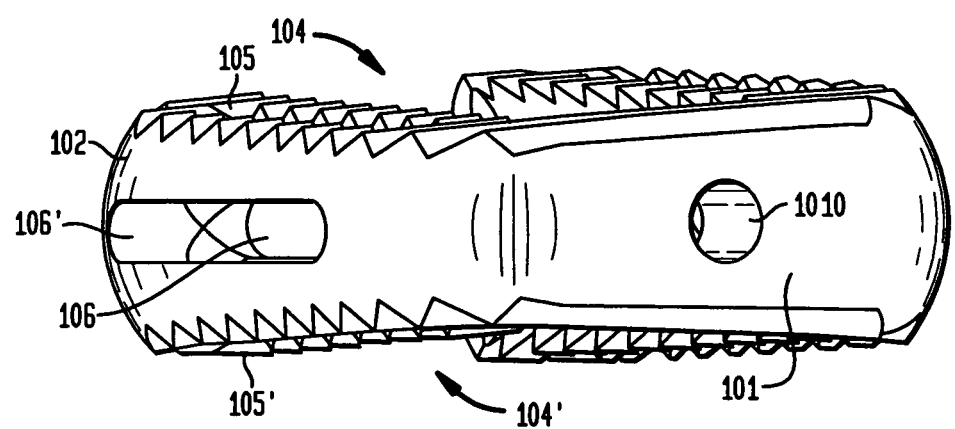
Figure 37:
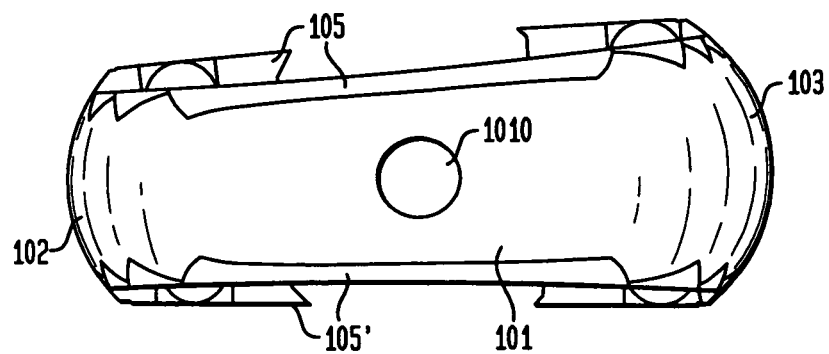
FIG. 37 is an end view, from the distal direction, of the body of FIGS. 34-36.
Figure 38:
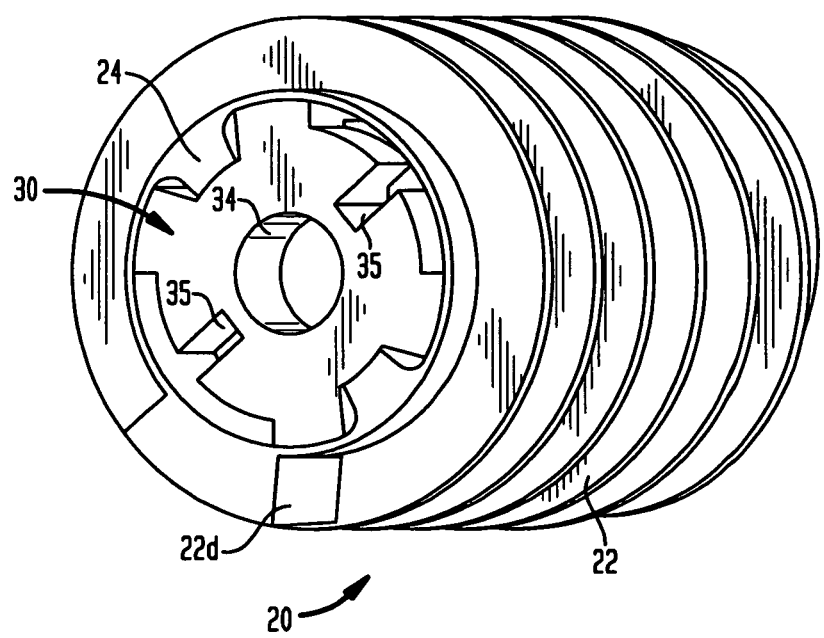
FIG. 38 is a perspective view of the anchorage reinforcement member of FIG. 33.
Figure 39:
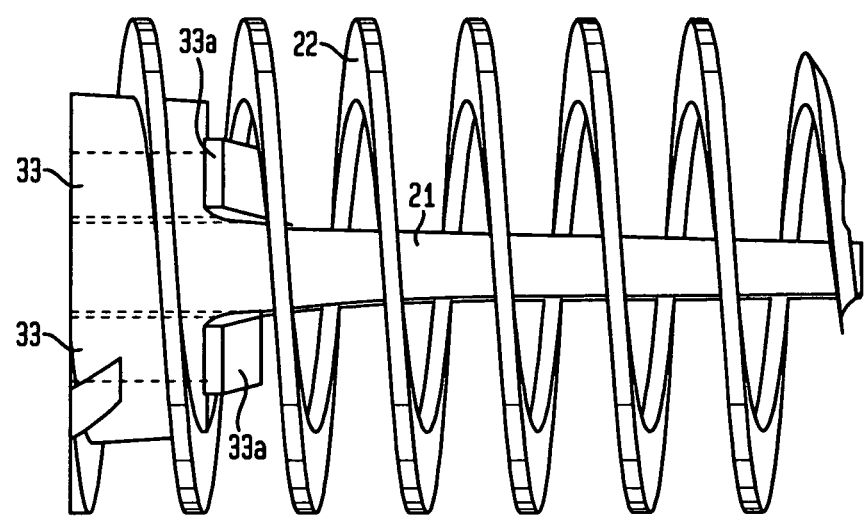
FIG. 39 is a side elevational view of the anchorage reinforcement member of FIG. 33.

Referring to FIGS. 33, 38 and 40, the end of the thread 22 on the proximal side is deformed, as indicated at 22d. The deformation is formed in the direction of the adjacent thread turn, that is to say towards the distal end.

This deformation makes it possible to give the thread 22 an immobilizing function against reverse rotation, and thus to prevent any risk of the anchorage reinforcement member 20 coming loose from the body 10 after fitting, but before bone fusion.

Referring to FIGS. 33 to 44, the implant is fitted in place by filling the openings 110 and 111 of the body 10 with material promoting bone growth, such as bone grafts. The body is then inserted into the intervertebral space, if necessary after distraction. The anchorage reinforcement member 20 is filled with a material promoting bone growth, and this member 20 is then closed at its proximal end by the plug 30 being clipped in. By means of screwing, the member is engaged in the already fitted body. The tapered shape of the two branches 21 of the fork makes it possible, as the member 20 advances, to compress the bone growth material and thus to ensure good contact with the overlying and underlying vertebral plateaus and with the bone growth material placed in the openings 110 and 111, via the openings 108 and 109.

The implants of the present invention are preferably made of a biocompatible material of suitable strength, such as a titanium alloy or stainless steel.

The surgeon is preferably offered implants according to the invention in the form of a set of implants of different shapes and dimensions, making it possible for a surgeon to choose an implant, and in particular the body 10, best suited to the anatomy of the implantation site.

Implants can be provided in which the bodies 10 have different heights. Because of the different body heights, the diameter of the member 20 may vary so that it works effectively with the selected body 10. Implants can also be provided in which the bodies have different widths. Thus, in the particular case of the third embodiment, it is possible to provide a range of implants whose widths vary progressively between a minimum width (e.g. FIGS. 16 to 19) and a maximum width (e.g. FIGS. 33 to 44), by varying the thickness, in the lateral direction, of the lateral branches 102 and 103 of the body, while at the same time maintaining the same size of internal space and also being able to use the same member 20 in all cases. These lateral branches 102, 103 preferably vary from a single wall (FIGS. 16 to 19) to a double wall (FIGS. 33 to 44) once the thickness of the branches 102, 103 has become sufficient to allow the vertical through-openings 110 and 111 to be made. Implants may also be provided whereby the bodies have upper and lower faces of different mutual inclinations, both from the front towards the rear and also laterally, with members 20 of identical or different diameters. Implants may also be provided whereby the bodies 10 and/or the anchorage reinforcement members 20 have different lengths, and in which the anchorage reinforcement members have different anchorage projections, and in particular of greater or lesser depth and greater or lesser spacing, depending on the mechanical characteristics encountered in the vertebral plateaus, etc.

The present invention is in no way limited to the embodiments described above and illustrated in the drawings, and one skilled in the art will be able to vary or modify the embodiments in accordance with the spirit of the invention, and in particular will be able to combine the particular features of the various embodiments described.

Furthermore, the bone anchorage projections such as have been described above can include any structure permitting mechanical anchorage and/or bone connection with the overlying and underlying vertebral plateaus. In particular, this can be a porous coating or hydroxyapatite.

The invention claimed is:

1. A spinal implant comprising:
    a hollow body having a leading end, an open trailing end and first and second lateral braches extending from said leading end to said open trailing end, said lateral branches including opposing concave, non-threaded inner surfaces defining an internal space of said hollow body and outer surfaces defining an outer dimension of said hollow body, said hollow body having upper and lower faces extending between said leading and trailing ends and along said first and second lateral branches, wherein said upper and lower faces are arranged to contact adjacent vertebral bodies, and said first and second lateral branches are spaced apart from one another so that each vertebral body is engageable with said first and second lateral branches at first and second distinct locations by way of said upper and lower faces;
    a first opening extending between said outer and inner surface of each lateral branch, and a second opening located outside said internal space of said hollow body and extending between said upper and lower faces and at least partially through said first lateral branch, at least one of said first openings being in communication with said second opening; and
    an anchoring member insertible between said lateral branches and into said internal space of said hollow body, said anchoring member having bone anchoring projections defining an outer diameter of said anchoring member, wherein said open trailing end of said hollow body is configured to allow insertion of said outer diameter of said anchoring member therethrough,
    and wherein when said anchoring member is inserted into said internal space of said hollow body, said concave inner surfaces of said lateral branches substantially surround said outer diameter of said anchoring member.

2. The implant as claimed in claim 1, wherein said hollow body has a distal wall extending between said lateral branches at said distal end thereof.

3. The implant as claimed in claim 2, wherein said distal wall has a threaded bore extending at least partially therethrough.

4. The implant as claimed in claim 2, wherein said distal wall has a curved outer surface that is located at said leading end of said hollow body.

5. The implant as claimed in claim 1, wherein said hollow body is U-shaped, and wherein said leading end is closed.

6. The implant as claimed in claim 1, wherein said internal space of said hollow body has a substantially cylindrical shape that is defined by said concave inner surfaces of said lateral branches.

7. The implant as claimed in claim 1, wherein said concave inner surfaces of said lateral branches define a curved opening at said open trailing end of said hollow body.

8. The implant as claimed in claim 1, wherein at least one of said lateral branches has a reentrant thread at said open trailing end of said hollow body.

9. The implant as claimed in claim 1, wherein said upper and lower faces of said hollow body are angled relative to one another between said leading end and said open trailing end of said hollow body.

10. The implant as claimed in claim 1, wherein at least one of said upper and lower faces of said hollow body has bone anchoring projections.

11. The implant as claimed in claim 10, wherein said hollow body has a longitudinal axis that extends between said leading end and said open trailing end and said bone anchoring projections on said hollow body extend in a direction that traverses said longitudinal axis of said hollow body.

12. The implant as claimed in claim 1, wherein said outer surfaces of said lateral branches are convex.

13. The implant as claimed in claim 1, wherein each of said lateral branches comprises an inner wall including said concave inner surface of said lateral branch and an outer wall spaced from said inner wall, said outer wall including said outer surface of said branch.

14. The implant as claimed in claim 13, wherein said inner wall of each said lateral branch has a cross-section that is C-shaped.

15. The implant as claimed in claim 1, wherein said bone anchoring projections of said anchoring member comprise threads.

16. The implant as claimed in claim 15, wherein said open trailing end of said hollow body has a curved opening that is bordered by a reentrant thread formed on at least one of said lateral branches and said threads of said bone anchoring member are adapted to cooperate with said reentrant thread for allowing said anchoring member to be screwed into said internal space of said hollow body.

17. The implant as claimed in claim 16, wherein said threads on said anchoring member define an external diameter and said concave inner surfaces of said lateral branches define an internal diameter of said hollow body that substantially surrounds said external diameter of said anchoring member.

18. The implant as claimed in claim 1, wherein said anchoring member has a hollow core and said bone anchoring projections of said anchoring member surround said hollow core.

19. The implant as claimed in claim 18, further comprising a bone growth inducing material provided in said hollow core of said anchoring member.

20. The implant as claimed in claim 1, further comprising a bone-growth inducing material provided in said internal space of said hollow body.

21. A spinal implant comprising:
a hollow body having a leading end, an open trailing end and first and second lateral branches extending between said leading end and said open trailing end, said lateral branches including concave, non-threaded inner surfaces that oppose one another for defining an inner diameter of said hollow body, said lateral branches having outer surfaces defining an outer dimension of said hollow body, said hollow body having upper and lower faces extending between said leading and trailing ends and along said first and second lateral branches, wherein said upper and lower faces are arranged to contact adjacent vertebral bodies, and said first and second lateral branches are spaced apart from one another so that each vertebral body is engageable with said first and second lateral branches at first and second distinct locations by way of said upper and lower faces;
a first opening extending between said outer surface and said concave inner surface of each lateral branch, and a second opening located outside an internal space of said hollow body and extending between said upper and lower faces and at least partially through said first lateral branch, at least one of said first openings being in communication with said second opening within said first lateral branch; and
an anchoring member insertible between said lateral branches of said hollow body, said anchoring member having threads defining an outer diameter of said anchoring member, wherein said open trailing end of said hollow body is configured to allow insertion of said outer diameter of said anchoring member therethrough, and wherein said outer diameter of said anchoring member substantially matches said inner diameter of said hollow body so that when said anchoring member is inserted into said hollow body, said concave inner surfaces of said lateral branches at least partially surround said outer diameter of said anchoring member.

22. The implant as claimed in claim 21, wherein said anchoring member has a hollow core surrounded by said threads of said anchoring member.

23. The implant as claimed in claim 22, further comprising a bone-growth inducing substance provided in said hollow core of said anchoring member.

* * * * *